United States Patent
Bremer et al.

(10) Patent No.: US 6,916,513 B2
(45) Date of Patent: Jul. 12, 2005

(54) 2,4'-SUBSTITUTED 6-CYCLOHEXYL-TRANS-DECALINES

(75) Inventors: Matthias Bremer, Darmstadt (DE); Detlef Pauluth, Darmstadt (DE); Georg Lüssem, Ober-Ramstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/474,330
(22) PCT Filed: Mar. 22, 2002
(86) PCT No.: PCT/EP02/03228

§ 371 (c)(1),
(2), (4) Date: Oct. 7, 2003

(87) PCT Pub. No.: WO02/081418

PCT Pub. Date: Oct. 17, 2002

(65) Prior Publication Data

US 2004/0119050 A1 Jun. 24, 2004

(30) Foreign Application Priority Data

Apr. 7, 2001 (DE) .......................... 101 17 559

(51) Int. Cl.[7] .................. C09K 19/32; C09K 19/30; C07C 22/00; C07C 43/192
(52) U.S. Cl. .............. 428/1.1; 252/299.62; 252/299.63; 570/130; 570/131; 570/187
(58) Field of Search .............. 428/1.1, 1.3; 252/299.62, 252/299.63; 570/130, 131, 187

(56) References Cited

U.S. PATENT DOCUMENTS

| | | | | |
|---|---|---|---|---|
| 4,432,885 A | * | 2/1984 | Petrzilka et al. | 252/299.61 |
| 6,541,082 B2 | * | 4/2003 | Lussem et al. | 428/1.1 |
| 2002/0027217 A1 | | 3/2002 | Lussem et al. | |
| 2004/0173774 A1 | * | 9/2004 | Heckmeier et al. | 252/299.63 |

FOREIGN PATENT DOCUMENTS

| | | |
|---|---|---|
| DE | 3150312 | 7/1982 |
| DE | 10112952 | 11/2001 |
| JP | 2000-355557 | * 12/2000 |
| JP | 2002-294236 | * 10/2002 |
| WO | WO 02/46329 | * 6/2002 |

OTHER PUBLICATIONS

English abstract for JP 2000–355557.*
English abstract for JP 2002–294236.*
CAPLUS 1985: 587304.*
Sucrow W. et al., "Flüssig–kristalline 2–Cyclohexyldecaline," Chemische Berichte, 1985, pp. 3350–3356, vol. 118, No. 8, XP002228536, ISSN: 0009–2940, cited in the application, the entire document, Verlag Chemie GmbH, Weinheim, DE.

* cited by examiner

*Primary Examiner*—Shean C. Wu
(74) *Attorney, Agent, or Firm*—Millen, White, Zelano, Branigan, P.C.

(57) ABSTRACT

The invention relates to 2,4'-substituted 6-cyclohexyl-trans-decalins of the general formula I

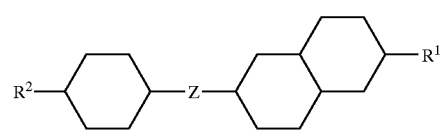

in which $R^1$, $R^2$ and Z are as defined in Claim 1, to the use thereof as components of liquid-crystalline media, and to a liquid-crystal display element and an electro-optical display element.

17 Claims, No Drawings

2,4'-SUBSTITUTED 6-CYCLOHEXYL-TRANS-DECALINES 2,4'-Subsdtituted 6-cyclohexyl-trans-decalins The invention relates to 2,4'-substituted 6-cyclohexyl-trans-decalins of the general formula I

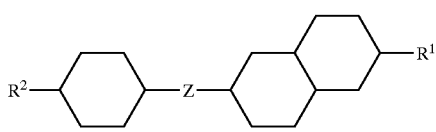

in which
- $R^1$ is halogen or alkyl having 1 to 18 carbon atoms, in which, in addition, one or two non-adjacent $CH_2$ groups may be replaced by —O—, —S—, —CO—, —O—CO—, —CO—O—, -E- and/or —C≡C— and in which at least one H atom is replaced by a halogen atom,
- $R^2$ is H, halogen, —CN or alkyl having 1 to 18 carbon atoms, in which, in addition, one or two non-adjacent $CH_2$ groups may be replaced by —O—, —S—, —CO—, —O—CO—, —CO—O—, -E- and/or —C≡C— and/or in which, in addition, one or more H atoms may be replaced by halogen,
- Z is a single bond, —$CH_2$O—, —O$CH_2$—, —COO—, —C≡C—, —CH=CH—, —$CF_2$O—, —O$CF_2$—, —CF=CF—, —$C_2F_4$—, —CH=CH—$(CH_2)_2$— or —$(CH_2)_4$—, and
- E is $CR^3$=$CR^4$ or $CHR^3$—$CHR^4$, and
- $R^3$, $R^4$ are each, independently of one another, H, alkyl having 1–6 carbon atoms, F, Cl, Br, $CF_3$ or CN.

The invention furthermore relates to the use of such compounds as components of liquid-crystalline media, to such a liquid-crystalline medium and to a liquid-crystal display element and an electro-optical display element.

DE 31 50 312 A1 discloses decalins of the above general formula, in which $R^2$ is methyl or one of the groups —$CH_2R'$, —OR', —CO—R', —CN, —COOH, —CO—OR', —CO—SR' or —O—CO—R'; $R^1$ is hydrogen, methyl or one of the groups —$CH_2R$, —OR, —$CH_2$OR or, when $R^2$ is methyl or one of the groups —$CH_2R'$, is additionally —CN, —COOH, —CO—OR, —CO—SR or —O—CO—R; R and R' are straight-chain or branched alkyl groups; $R^1$ and $R^2$ are identical or different; and the substituents $R^1$ and $R^2$ each have up to 12 carbon atoms and together have at most 14 carbon atoms. These mesogenic compounds are said to be useful in liquid-crystal mixtures.

In Helvetica Chimica Acta, Vol. 65, Fasc. 4 (1982), pages 1242–1257, M. Petrzilka and K. Schleich describe the synthesis of alkyl-substituted 2-phenyl- and 2-cyclohexyl-trans-decalins and their properties. The 2-cyclohexyl-trans-decalins are prepared from the corresponding 2-phenyl-cyclohexyl-trans-decalins bearing an alkylketone group in 4' position by hydrogenation, subsequent Jones oxidation with equlibration of the resulting trans-ketones and finally Huang-Minlon reduction to form the alkyl-substituted compound. The compounds obtained in this way have broad mesophase ranges and high N-I transition temperatures.

In Chem. Ber. 118, (1985) 3350–3356, W. Sucrow and H. Wolter describe the synthesis of 6-(4'-propyl-cyclohexyl)-trans-decalin-2-ol from 4-(trans-4'-propylcyclohexyl)-cyclohexanone. Transition temperatures of the mesogenic phases were given for the decalin-2-ol esters and ethers.

It is an object of the present invention to broaden the range of 2,4'-substituted 6-cyclohexyl-trans-decalins available for liquid-crystal mixtures, and in particular to provide substances which have a high dielectric anisotropy and a low birefringence. It is another object of this invention to indicate uses of such compounds.

These objects are achieved according to Claim 1 by 2,4'-substituted 6-cyclohexyl-trans-decalins of the formula I.

The novel decalins of the formula I exhibit a combination of high dielectric anisotropy and low birefringence which is particularly useful for liquid-crystal mixtures in electro-optical display elements. The compounds according to the invention typically have a dielectric anisotropy $\Delta\epsilon \geqq 4.0$ and an optical anisotropy $\Delta n \leqq 0.07$. Moreover, smectic phases are advantageously suppressed compared to known compounds having a similar basic structure. Futhermore, the compounds according to the invention exhibit a good miscibility with other liquid-crystalline compounds.

$R^2$ is preferably H, fluorine, chlorine, —CN, alkyl having 1–12 carbon atoms, in which, in addition, one or two non-adjacent $CH_2$ groups may be replaced by —O—, —CO—, —O—CO—, —CO—O—, -E- and/or —C≡C— and/or in which, in addition, one or more H atoms may be replaced by fluorine and/or chlorine.

$R^2$ is paricularly preferably H, methyl, ethyl, n-propyl, n-butyl, n-pentyl, n-hexyl, n-heptyl, n-octyl, vinyl, 1-propenyl, allyl, 1-butenyl, 2-butenyl, 3-butenyl, 3-pentenyl, 4-pentenyl, 1,5-hexadienyl, methoxy, ethoxy, n-propoxy, n-butoxy, n-pentoxy, n-hexoxy, vinyloxy, 1-propenyloxy, 2-propenyloxy, 2-butenyloxy, methoxy-methylene, 2-methoxy-ethylene, 3-methoxy-propylene, 4-methoxy-butylene, 5-methoxy-pentylene, ethoxy-methylene, 2-ethoxy-ethylene, etheneoxy-methylene, 2-etheneoxy-ethylene, in which, in addition, one or more H atoms may be replaced by fluorine.

$R^1$ and/or $R^2$ are preferably, independently of one another, alkyl, alkenyl, alkoxy, alkenyloxy, oxaalkyl or oxaalkenyl having 1 to 8 carbon atoms, where, in $R^1$, at least one H atom is substituted by a halogen atom.

If $R^1$ and/or $R^2$ is an alkyl radical, this can be straight-chain or branched. It is preferably straight-chain and accordingly is in particular methyl, ethyl, n-propyl, n-butyl, n-pentyl, n-hexyl, n-heptyl or n-octyl.

If $R^1$ and/or $R^2$ is an alkenyl radical, this can be straight-chain or branched. It is preferably straight-chain and has 2 to 8 carbon atoms. Accordingly, it is in particular vinyl, prop-1- or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl or oct-1-, 2-, 3-, 4-, 5-, 6- or oct-7-enyl.

If $R^1$ and/or $R^2$ is an alkoxy radical, this can be straight-chain or branched. It is preferably straight-chain and accordingly is in particular methoxy, ethoxy, n-propoxy, n-butoxy, n-pentoxy, n-hexoxy, n-heptoxy or n-octoxy.

If $R^1$ and/or $R^2$ is an alkenyloxy radical, this can be straight-chain or branched. It is preferably straight-chain and accordingly is in particular vinyloxy, prop-1- or prop-2-enyloxy, but-1-, 2- or but-3-enyloxy, pent-1-, 2-, 3- or pent-4-enyloxy, hex-1-, 2-, 3-, 4- or hex-5-enyloxy, hept-1-, 2-, 3-, 4-, 5- or hept-6-enyloxy or Oct-1-, 2-, 3-, 4-, 5-, 6- or Oct-7-enyloxy.

If $R^1$ and/or $R^2$ is an oxaalkyl radical, this can be straight-chain or branched. It is preferably straight-chain and accordingly is in particular 2-oxapropyl (=methoxymethyl), 2- (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl or 2-, 3-, 4-, 5-, 6- or 7-oxaoctyl.

If $R^1$ and/or $R^2$ is an oxaalkenyl radical, this can be straight-chain or branched. It is preferably straight-chain and accordingly is in particular 3-oxabut-1-enyl (=methoxyvinyl), 2-oxabut-3-enyl (=vinyloxymethyl), 4-oxapent-1-enyl (=methoxyprop-1-enyl), 3-oxapent-1-enyl (=ethoxyvinyl), 4-oxapent-2-enyl (=methoxyprop-2-enyl), 2-oxapent-3-enyl (=prop-1-enoxymethyl), 2-oxapent-4-enyl (=prop-2-enoxymethyl), 3-oxapent-4-enyl (=vinyloxyethyl), 3-oxahex-1-enyl, 4-oxahex-1-enyl, 5-oxahex-1-enyl, 4-oxahex-2-enyl, 5-oxahex-2-enyl, 2-oxahex-3-enyl, 5-oxahex-3-enyl, 2-oxahex-4-enyl, 3-oxahex-4-enyl, 2-oxahex-5-enyl, 3-oxahex-5-enyl or 4-oxahex-5-enyl.

In each of the abovementioned meanings of $R^1$ as alkyl, alkenyl, alkoxy, alkenyloxy, oxaalkyl or oxaalkenyl, at least one H atom is substituted by a halogen atom, preferably by fluorine and/or chlorine, particularly preferably by fluorine. Preferably, 2 or more H atoms are substituted by fluorine. Particularly preferably, 2 or 3 H atoms in the terminal methyl group are replaced by fluorine in the abovementioned radicals so that the abovementioned radicals have a $CHF_2$ or a $CF_3$ group. Particularly preferably, the whole radical $R^1$ is perfluorinated.

Particularly preferred fluorinated alkyl radicals $R^1$ are —$CHF_2$, —$CF_3$, —$CH_2CHF_2$, —$CH_2CF_3$, —$CF_2CHF_2$, —$CF_2CF_3$, —$CH_2CH_2CHF_2$, —$CH_2CH_2CF_3$, —$CH_2CF_2CHF_2$, —$CH_2CF_2CF_3$, —$CF_2CH_2CHF_2$, —$CF_2CH_2CF_3$, —$CF_2CF_2CHF_2$, —$CF_2CF_2CF_3$, —$C_2F_5$, —$C_3F_7$, —$C_4F_9$, —$C_5F_{11}$, —$C_6F_{13}$, —$C_7F_{15}$ or —$C_8F_{17}$.

Particularly preferred fluorinated alkenyl radicals $R^1$ are —CH=CHF, —CH=$CF_2$, —CF=$CF_2$, —CH=$CHCF_3$, —CH=CF—$CF_3$, —CF=$CFCF_3$, —$CH_2$—CH=CHF, —$CH_2$—CH=$CF_2$, —$CF_2$—CH=$CH_2$, —$CF_2$—CH=CHF, —$CF_2$—CH=$CF_2$, —$CF_2$—CF=$CF_2$ or —$CF_2$—CF=$CFCF_3$.

Particularly preferred fluorinated alkoxy radicals $R^1$ are —$OCHF_2$, —$OCF_3$, —$OCH_2CHF_2$, —$OCH_2CF_3$, —$OCF_2CHF_2$, —$OCF_2CF_3$, —$OCH_2CH_2CHF_2$, —$OCH_2CH_2CF_3$, —$OCH_2CF_2CHF_2$, —$OCH_2CF_2CF_3$, —$OCF_2CH_2CHF_2$, —$OCF_2CH_2CF_3$, —$OCF_2CF_2CHF_2$, —$OCF_2CF_2CF_3$, —$OC_4F_9$, —$OC_5F_{11}$, —$OC_6F_{13}$, —$OC_7F_{15}$ or —$OC_8F_{17}$.

Particularly preferred fluorinated alkenyloxy radicals $R^1$ are —OCH=CHF, —OCH=$CF_2$, —OCF=$CF_2$, —OCH=$CHCF_3$, —OCH=CF—$CF_3$, —OCF=$CFCF_3$, —$OCH_2$—CH=CHF, —$OCH_2$—CH=$CF_2$, —$OCH_2$—CF=$CF_2$, —$OCF_2$—CH=$CH_2$, —$OCF_2$—CH=CHF, —$OCF_2$—CH=$CF_2$, —$OCF_2$—CF=$CF_2$, —$OCH_2$—CH=$CHCF_3$, —$OCF_2$—CH=$CHCH_3$, —$OCF_2$—CH=$CHCF_3$ or —$OCF_2$—CF=$CFCF_3$.

Particularly preferred fluorinated oxaalkyl radicals $R^1$ are —$CH_2OCHF_2$, —$CH_2OCF_3$, —$CF_2OCH_3$, —$CF_2OCHF_2$, —$CF_2OCF_3$, —$CH_2OCH_2CHF_2$, —$CH_2OCH_2CF_3$, —$CH_2OCF_2CF_3$, —$CF_2OCH_2CF_3$ or —$CF_2OCF_2CF_3$.

Particularly preferred fluorinated oxaalkenyl radicals $R^1$ are —$CH_2$OCH=CHF, —$CH_2$OCH=$CF_2$, —$CH_2$OCF=$CF_2$, —$CF_2$OCH=$CH_2$, —$CF_2$OCH=CHF, —$CF_2$OCH=$CF_2$, —$CF_2$OCF=$CF_2$, —$CH_2$OCH=$CHCF_3$, —$CH_2$OCH=$CFCF_3$, —$CH_2$OCF=$CFCF_3$, —$CF2$OCH=$CHCH_3$, —$CF_2$OCH=$CHCF_3$, —$CF_2$OCH=$FCF_3$ or —$CF_2$OCF=$CFCF_3$.

Z is preferably a single bond, further —$C_2F_4$—.

Particularly preferred novel compounds of the formula I are listed below, n being from 1 to 6:

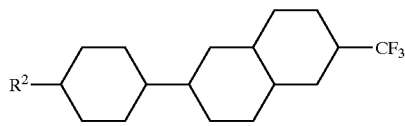

I.1

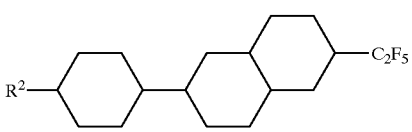

I.2

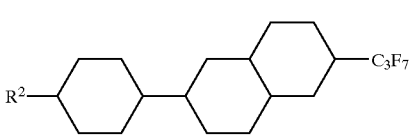

I.3

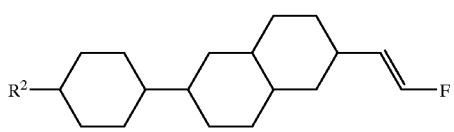

I.4

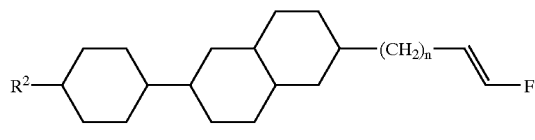

I.5

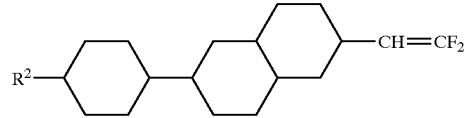

I.6

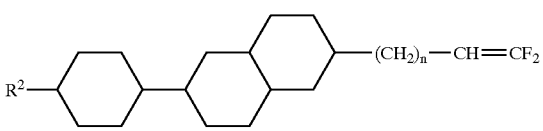

I.7

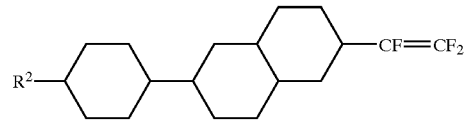

I.8

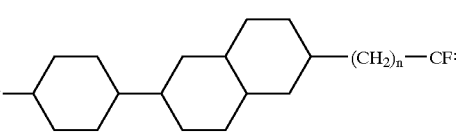

I.9

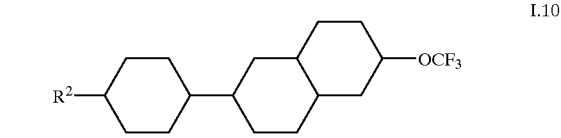

I.10

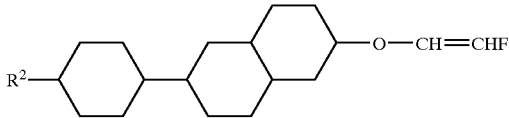

I.11

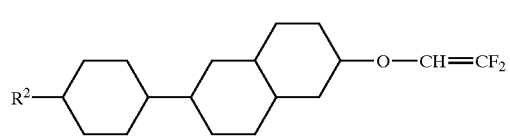

I.12

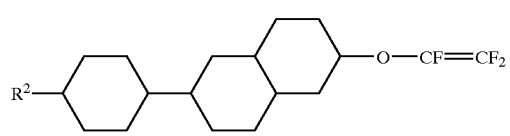

I.13

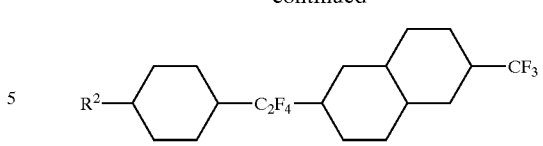

I.14

Here, R² is as defined above, in particular methyl, ethyl, n-propyl, n-butyl, n-pentyl, n-hexyl or n-heptyl.

Above and below, cyclohexylene groups in the compounds according to the invention and in further compounds used in liquid-crystalline media are preferably trans-substituted.

The novel compounds of the formula 1, in particular of the formulae I.1 to I.3 and I.10, can advantageously be prepared in accordance with the following scheme.

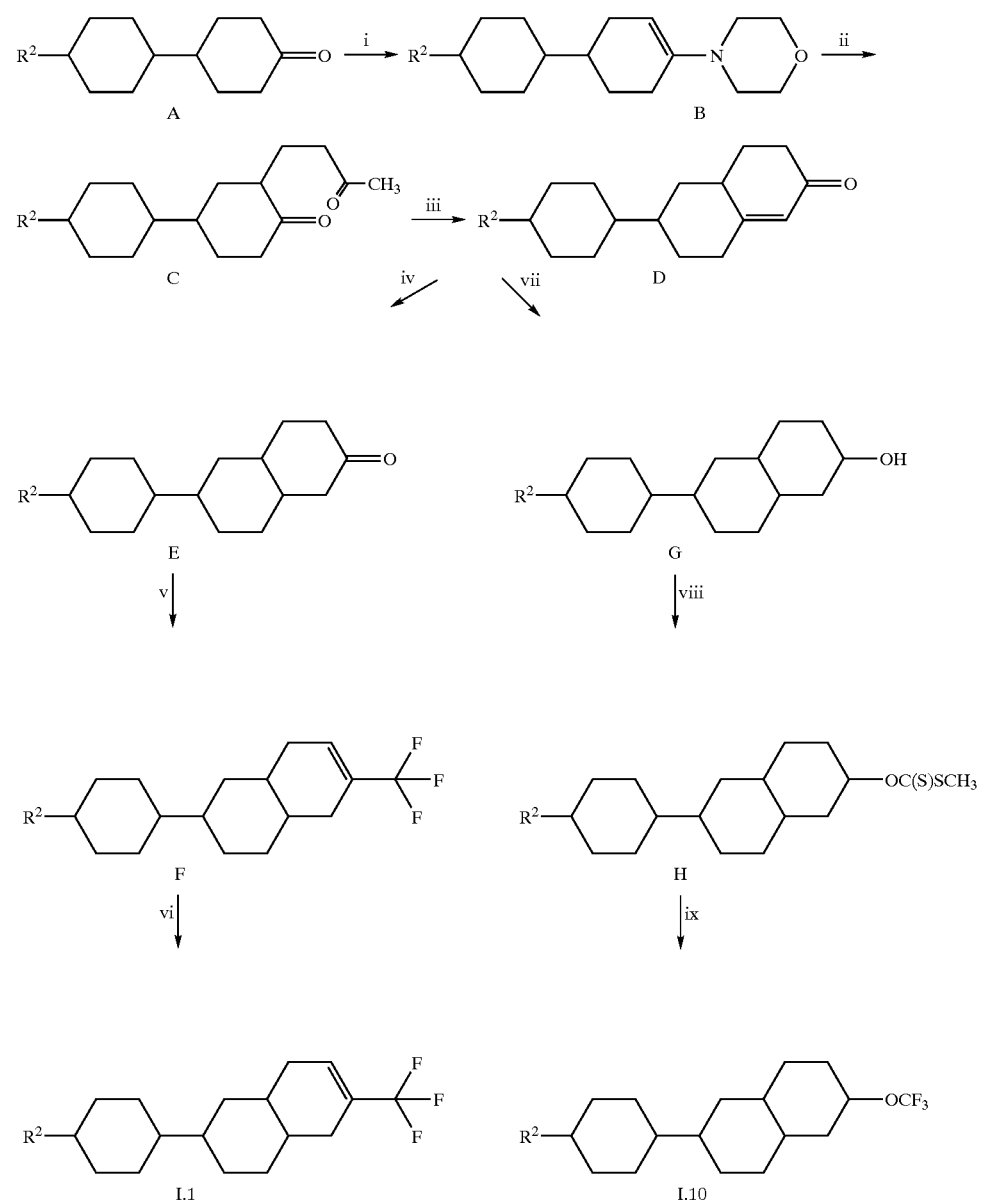

Compounds of the formula I having a —C$_2$F$_4$— bridge can be prepared, for example, as follows.

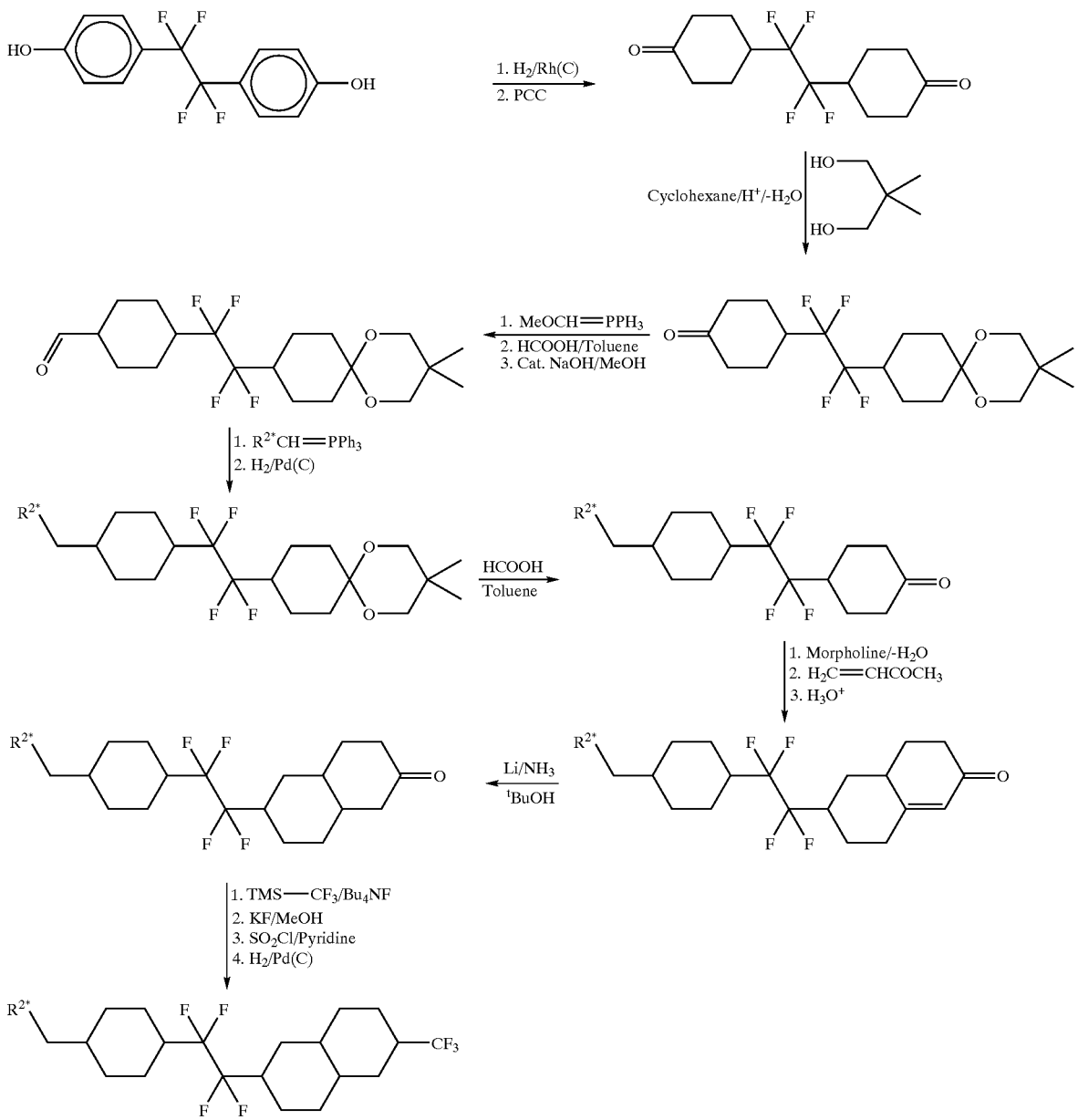

Scheme 2

R$^{2*}$ in Scheme 2 is H, halogen, CN or alkyl having 1 to 17 carbon atoms, in which, in addition, one or two non-adjacent CH$_2$ groups may be replaced by —O—, —S—, —CO—, —O—CO—, —CO—O—, -E- and/or —C≡C— and/or in which, in addition, one or more H atoms may be replaced by halogen.

The starting trans-substituted cyclohexyl-cyclohexanone of the formula A is converted into the corresponding enamine (B) in Step i, using morpholine, and the enamine is alkylated by means of methyl vinyl ketone to form the ketone compound of the formula C in Step ii. In the subsequent Step iii, a cyclization to give the substituted decalinenone of the formula D is performed. As regards the formation of the desired trans-decalin skeleton by forming the desired stereoisomer of compound C at an elevated temperature in an acidic medium and/or by base-catalyzed cyclization, reference is made to the article by W. Sucrow and H. Wolter (loc. cit.).

The 4'-substituted 2-trifluoromethyl-6-cyclohexyl-trans-decalin of the formula I.1 can be obtained from the decalinenone (D) via the corresponding decalinone (E). To this end, a Birch reduction is conducted in Step iv, preferably using lithium in liquid ammonia and tert.-butyl alcohol, followed by Jones oxidation of the secondary alcohol formed. In Step v, the ketone E is first reacted with trimethylsilyltrifluoromethane and tetrabutylammonium fluoride, followed by addition of potassium fluoride in methanol and finally dehydration by means of thionyl chloride (SOCl$_2$) in pyridine. In Step vi, the resulting decalinene (F) is finally hydrogenated in the presence of palladium on activated carbon to form the desired compound I.1.

Alternatively, the 4'-substituted 2-trifluoromethoxy-6-cyclohexyl-trans-decalin of the formual I.10 can be obtained from the decalinenone (D) via the decalinol (G) and further via the compound of the formula H. In the first Step vii, the trans-decalinol (G) is obtained by Birch reduction in two steps as described by W. Sucrow and H. Wolter (loc. cit.). The subsequent steps viii and ix are conducted in accordance with the synthetic route which was described by Kiyoshi et al. in Chem. Lett. 1997, 827–828, and exemplified by the reaction of cyclohexanone to form trifluoromethoxy-cyclohexanone. Accordingly, compound H is obtained in Step viii by reaction with a hydrogenating agent, such as sodium hydride, carbon disulphide ($CS_2$) and dimethyl sulphate. Further reaction with hydrogen fluoride in pyridine and finally with N-bromosuccinimide (NBS) in dichloromethane ($CH_2Cl_2$) leads to the desired trifluoromethoxy-decalin (I.10).

Futhermore, the novel compounds of the formula I, in particular of the formulae I.4 to I.9, can be prepared in accordance with the following scheme.

In Step xiii, the decalinol of the formula G is reacted with formic acid and dicyclohexylcarbodiimide, advantageoulsy in the presence of 4-dimethyl-aminopyridine to obtain compound L. In Step xiv, the attachment of a difluoromethyl group to the aldehyde L is advantageously performed using dibromodifluoromethane and hexamethyltriaminophosphine to obtain the difluorovinyloxy compound I.11.

Suitable reaction conditions, such as pressure, temperature, reation times and solvents, for each of the abovementioned synthetic steps are known to the person skilled in the art at least from similar reactions or can easily be derived from similar reactions and optimized by simple experiments. For example, the conditions for carrying out individual synthetic steps of at least similar reactions are known by W. Sucrow and H. Wolter (loc. cit.) and Kiyoshi et al. (loc. cit.).

Other novel compounds of the formula I can be obtained in analogy to the above synthetic scheme, if necessary with the inclusion of further synthetic steps known to the person skilled in the art.

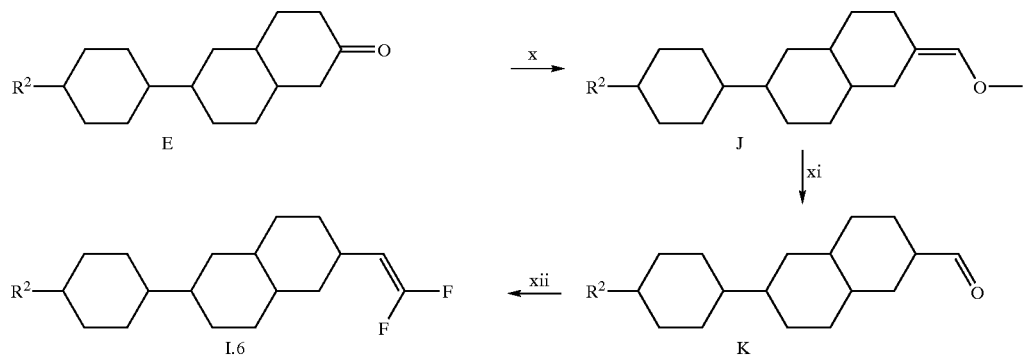

In Step x, the decalinone of the formula E is reacted with methoxymethyl-triphenylphosphonium bromide in an alkaline medium to form the methyl vinyl ether J, which is cleaved in an acidic medium to give the aldehyde K. The aldehyde K is reacted with sodium chlorodifluoroacetate and triphenylphosphine to obtain the difluorovinyl compound I.6.

In addition, the novel compounds of the formula I, in particular of the formulae I.11 to I.13, can be prepared in accordance with the following scheme.

As an alternative to the above synthetic scheme, the novel compounds of the formula I can also be obtained by constructing a 2,4'-substituted 6-phenyl-trans-decalin skeleton and subsequent hydrogenation to form the corresponding 6-cyclohexyl-trans-decalin and, if desired, further functionalization. In this regard, reference is explicitly made to the publications by M. Petrzilka and K. Schleich (loc. cit. and DE 31 50 312 A1).

The liquid-crystalline media according to the invention preferably contain 2 to 40, in particular 4 to 30, components as further constituents besides one or more compounds

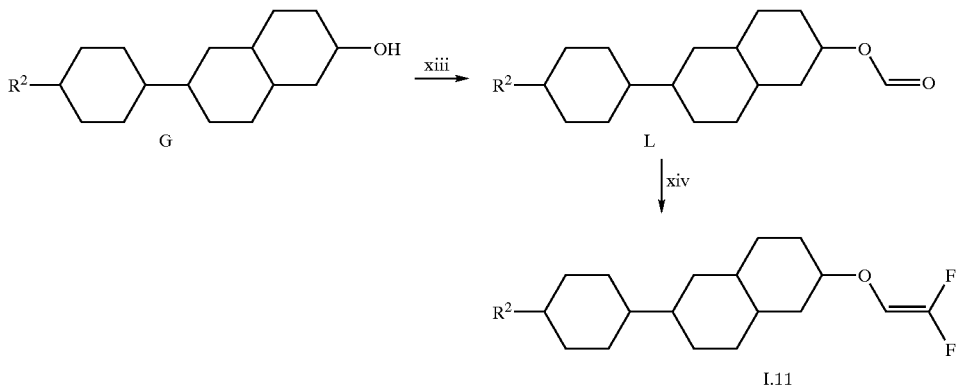

according to the invention. These media very particularly preferably contain 7 to 25 components besides one or more compounds according to the invention. These further constituents are preferably selected from nematic or nematogenic (monotropic, enantiotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexyl-benzoic acid, phenyl or cyclohexyl esters of cyclohexyl-cyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-bis-cyclohexylbenzenes, 4,4'-bis-cyclohexylbiphenyls, phenyl- or cyclohexyl-pyrimidines, phenyl- or cyclohexylpyridines, phenyl- or cyclohexyldioxanes, phenyl- or cyclohexyl-1,3-dithianes, 1,2-diphenylethanes, 1,2-dicyclohexyl-ethanes, 1-phenyl-2-cyclohexylethanes, 1-cyclohexyl-2-(4-phenyl-cyclohexyl)ethanes, 1-cyclohexyl-2-biphenylylethanes, 1-phenyl-2-cyclohexylphenylethanes optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterized by the formulae 1, 2, 3, 4 and 5:

| | |
|---|---|
| R'-L-E-R" | 1 |
| R'-L-COO-E-R" | 2 |
| R'-L-OOC-E-R" | 3 |
| R'-L-CH$_2$CH$_2$-E-R" | 4 |
| R'-L-C≡C-E-R" | 5 |

In the formulae 1, 2, 3, 4 and 5, L and E, which may be identical or different, are in each case, independently of one another, a bivalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclo-hexylene or 1,4-cyclahexylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably contain one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group consisting of -Phe-Cyc-, -Cyc-Cyc-, -G-Phe- and -G-Cyc-.

In a smaller sub-group of the compounds of the formulae 1, 2, 3, 4 and 5, R' and R" are in each case, independently of one another, alkyl, alkenyl, alkoxy, alkoxyalkyl, alkenyloxy or alkanoyloxy having up to 8 carbon atoms. This smaller sub-group is referred to as group A below, and the compounds are labelled with the sub-formulae 1a, 2a, 3a, 4a and 5a. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5 which is referred to as group B, R" is —F, —Cl, —NCS or —(O)$_i$CH$_{3-(k+l)}$F$_k$Cl$_l$, where i is 0 or 1, and k+l is 1, 2 or 3; the compounds in which R" has this meaning are labelled with the sub-formulae 1b, 2b, 3b, 4b and 5b. Particular preference is given to those compounds of the sub-formulae 1b, 2b, 3b, 4b and 5b in which R" is —F, —Cl, —NCS, —CF$_3$, —OCHF$_2$ or —OCF$_3$.

In the compounds of the sub-formulae 1b, 2b, 3b, 4b and 5b, R' is as defined for the compounds of the sub-formulae 1a–5a and is preferably alkyl, alkenyl, alkoxy or alkoxyalkyl.

In a further smaller sub-group of the compounds of the formulae 1, 2, 3, 4 and 5, R" is —CN; this sub-group is referred to as group C below, and the compounds of this sub-group are correspondingly described by sub-formulae 1c, 2c, 3c, 4c and 5c. In the compounds of the sub-formulae 1c, 2c, 3c, 4c and 5c, R' is as defined for the compounds of the sub-formulae 1a–5a and is preferably alkyl, alkoxy or alkenyl.

In addition to the preferred compounds of groups A, B and C, other compounds of the formulae 1, 2, 3, 4 and 5 having other variants of the proposed substituents are also customary. All these substances can be obtained by methods which are known from the literature or analogously thereto.

Besides novel compounds of the formula I, the media according to the invention preferably contain one or more compounds selected from group A and/or group B and/or group C. The proportions by weight of the compounds from these groups in the media according to the invention are preferably Gruppe A: 0 to 90%, preferably 20 to 90%, in particular 30 to 90%

Gruppe B: 0 to 80%, preferably 10 to 80%, in particular 10 to 65%

Gruppe C: 0 to 80%, preferably 5 to 80%, in particular 5 to 50%, the sum of the proportions by weight of the group A and/or B and/or C compounds present in the particular media according to the invention preferably being 5% to 90% and in particular 10% to 90%.

The media according to the invention preferably comprise 1 to 40%, particularly preferably 5 to 30%, of compounds according to the invention. Further preferred media are those which comprise more than 40%, in particular 45 to 90%, of compounds according to the invention. The media preferably comprise two, three, four or five compounds according to the invention.

The novel media are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980).

For example, pleochroic dyes can be added for the production of coloured guest-host systems, or substances can be added to modify the dielectric anisotropy, the viscosity and/or the orientation of the nematic phases.

In the present application and especially in the examples below, the structures of the liquid-crystalline compounds are indicated by abbreviations also called acronyms. The transformation of the abbreviations into the corresponding structures is straightforward according to the two Tables A and B below. The groups $C_nH_{2n+1}$ and $C_mH_{2m+1}$ are straight-chain alkyl groups having n or m carbon atoms respectively. The interpretation of Table B is self-evident. In Table A, only the acronym for the parent structure is given. The individual compounds are denoted by the acronym for the parent structure followed by a hyphen and a code specifying the substituents $R^1$, $R^2$, $L^1$ and $L^2$ in accordance with the following list:

| Code for $R^1$, $R^2$, $L^1$, $L^2$ | $R^1$ | $R^2$ | $L^1$ | $L^2$ |
|---|---|---|---|---|
| Nm | $C_nH_{2n+1}$ | $C_mH_{2m+1}$ | H | H |
| NOm | $C_nH_{2n+1}$ | $OC_mH_{2m+1}$ | H | H |
| NO.m | $OC_nH_{2n+1}$ | $C_mH_{2m+1}$ | H | H |
| NO.Om | $OC_nH_{2n+1}$ | $OC_mH_{2m+1}$ | H | H |
| N | $C_nH_{2n+1}$ | CN | H | H |
| nN.F | $C_nH_{2n+1}$ | CN | H | F |
| nN.F.F | $C_nH_{2n+1}$ | CN | F | F |
| NF | $C_nH_{2n+1}$ | F | H | H |
| NF.F | $C_nH_{2n+1}$ | F | H | F |
| NF.F.F | $C_nH_{2n+1}$ | F | F | F |
| NOF | $OC_nH_{2n+1}$ | F | H | H |
| NCl | $C_nH_{2n+1}$ | Cl | H | H |
| NCl.F | $C_nH_{2n+1}$ | Cl | H | F |
| NCl.F.F | $C_nH_{2n+1}$ | Cl | F | F |
| $NCF_3$ | $C_nH_{2n+1}$ | $CF_3$ | H | H |
| $NCF_3.F$ | $C_nH_{2n+1}$ | $CF_3$ | H | F |
| $NCF_3.F.F$ | $C_nH_{2n+1}$ | $CF_3$ | F | F |
| $NOCF_3$ | $C_nH_{2n+1}$ | $OCF_3$ | H | H |
| $NOCF_3.F$ | $C_nH_{2n+1}$ | $OCF_3$ | H | F |
| $NOCF_3.F.F$ | $C_nH_{2n+1}$ | $OCF_3$ | F | F |
| $NOCF_2$ | $C_nH_{2n+1}$ | $OCHF_2$ | H | H |
| $NOCF_2.F$ | $C_nH_{2n+1}$ | $OCHF_2$ | H | F |
| $NOCF_2.F.F$ | $C_nH_{2n+1}$ | $OCHF_2$ | F | F |
| NS | $C_nH_{2n+1}$ | NCS | H | H |
| NS.F | $C_nH_{2n+1}$ | NCS | H | F |
| NS.F.F | $C_nH_{2n+1}$ | NCS | F | F |
| RVsN | $C_rH_{2r+1}$—CH=CH—$C_sH_{2s}$— | CN | H | H |
| REsN | $C_rH_{2r+1}$—O—$C_sH_{2s}$— | CN | H | H |
| NAm | $C_nH_{2n+1}$ | $COOC_mH_{2m+1}$ | H | H |

TABLE A

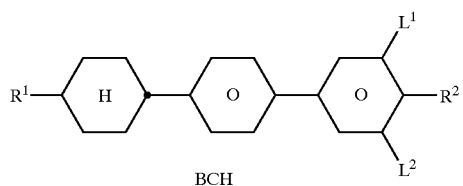

BCH

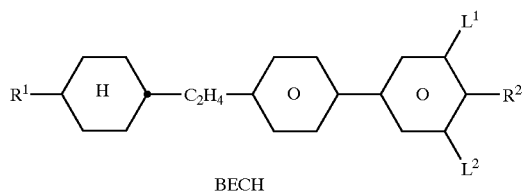

BECH

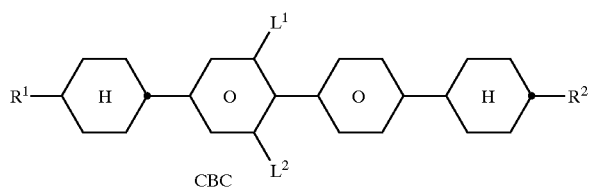

CBC

TABLE A-continued
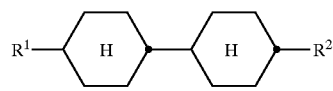
CCH
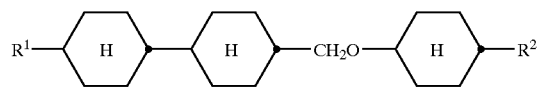
CCOC
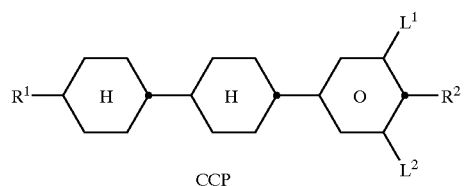
CCP
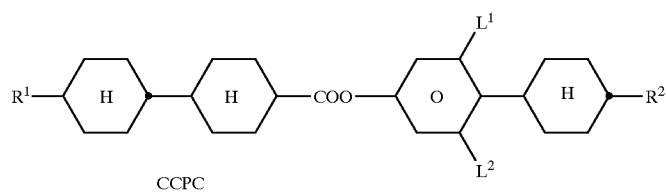
CCPC
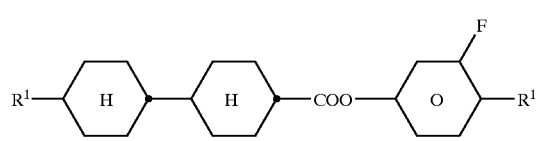
CCZG
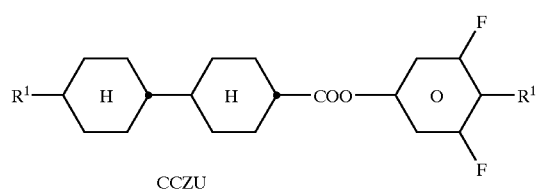
CCZU
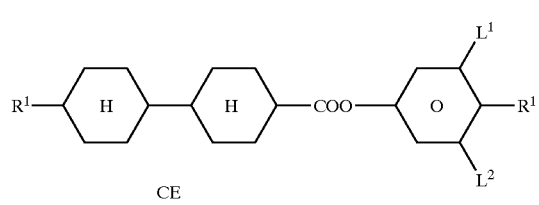
CE
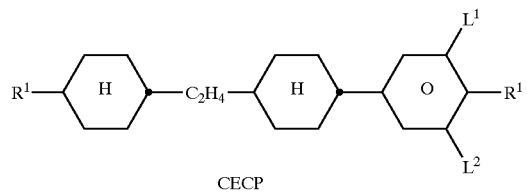
CECP TABLE A-continued
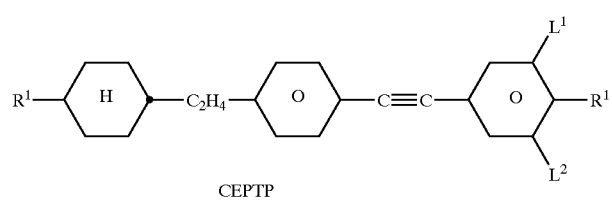
CEPTP
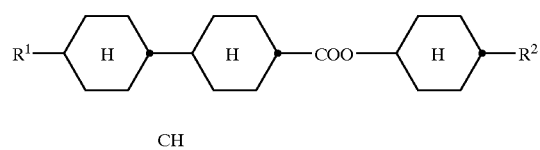
CH
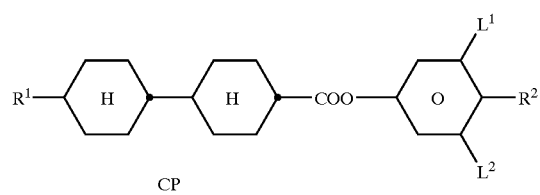
CP
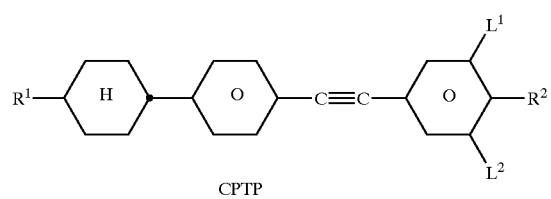
CPTP
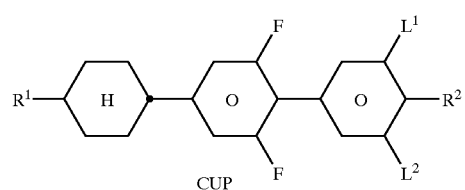
CUP
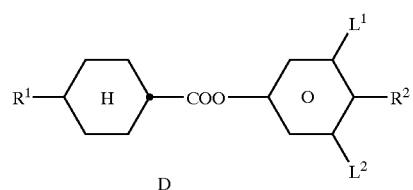
D
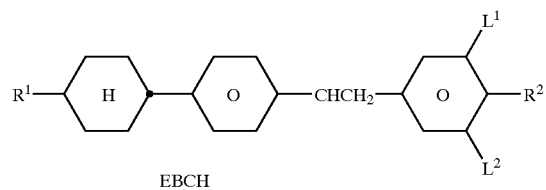
EBCH
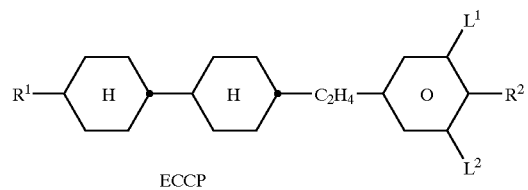
ECCP TABLE A-continued
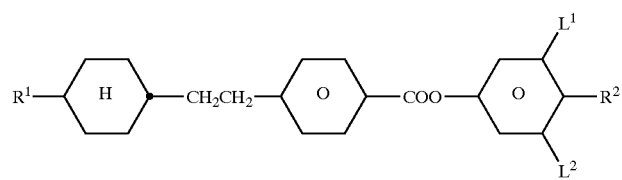
EHP
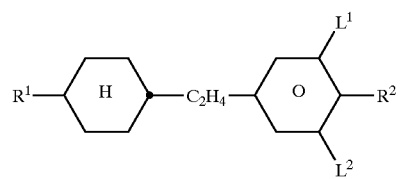
EPCH
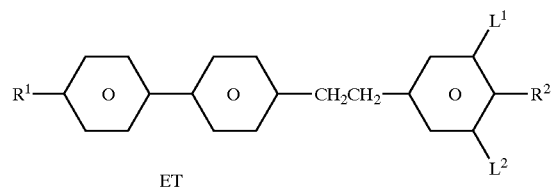
ET
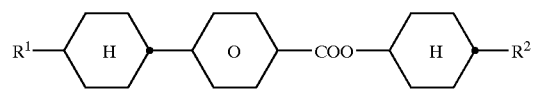
HD
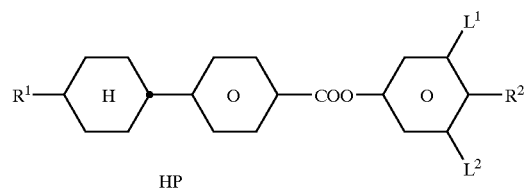
HP
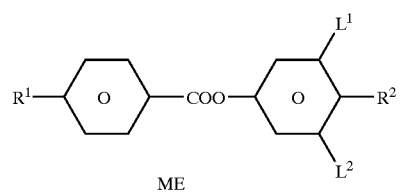
ME
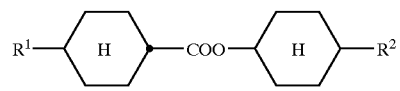
OS
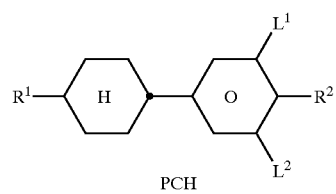
PCH TABLE A-continued
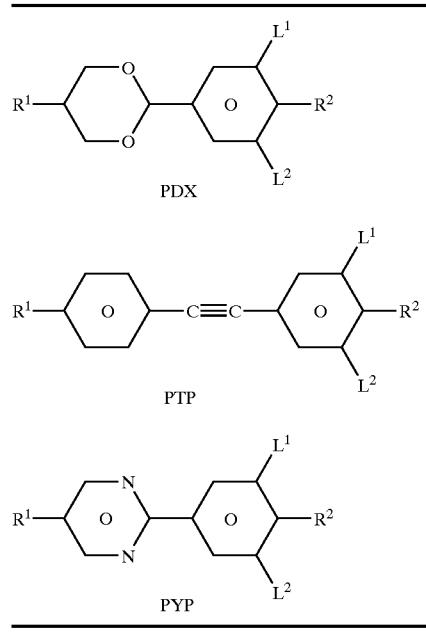
TABLE B
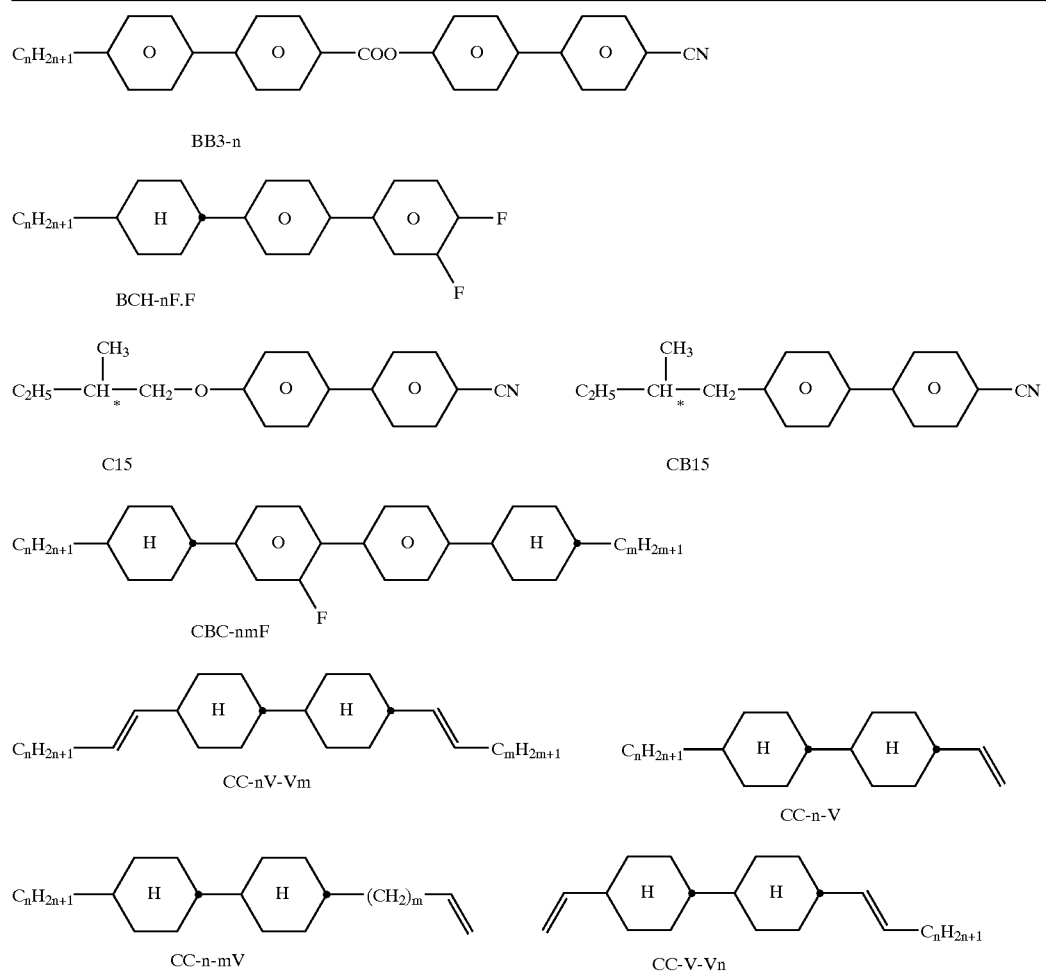

TABLE B-continued
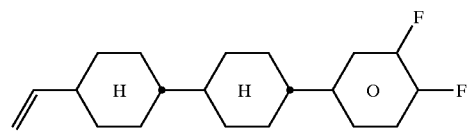
CCG-V-F
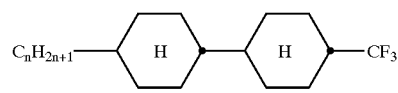
CCH-nCF₃
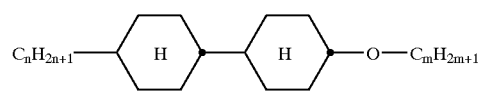
CCH-nOm
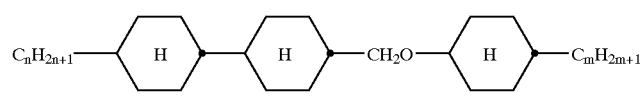
CCOC-n-m
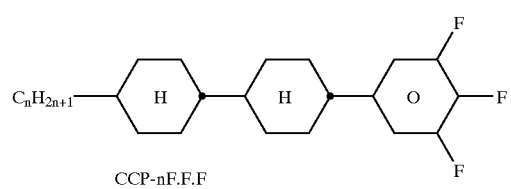
CCP-nF.F.F
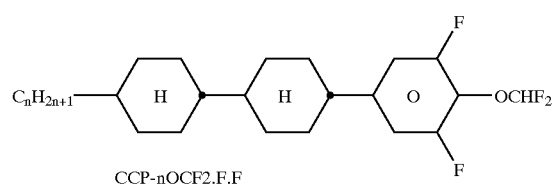
CCP-nOCF2.F.F
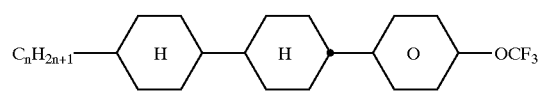
CCP-nOCF₃
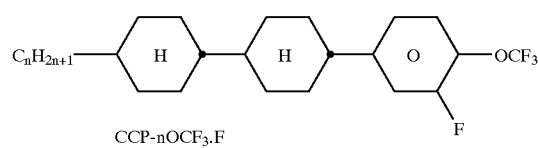
CCP-nOCF₃.F
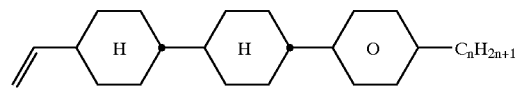
CCP-V-m TABLE B-continued
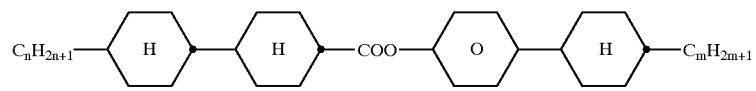
CCPC-nm
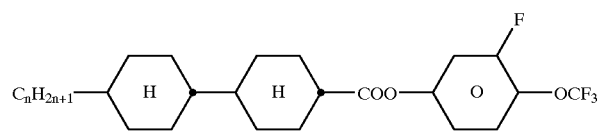
CCZG-n-OT
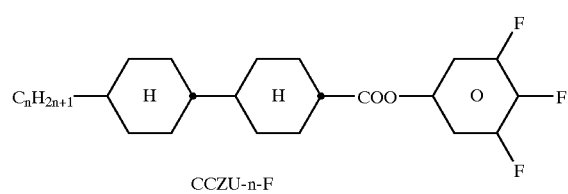
CCZU-n-F
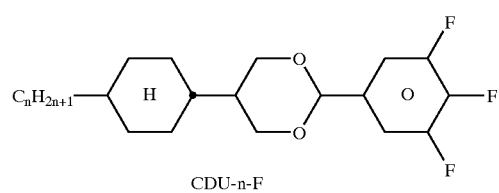
CDU-n-F
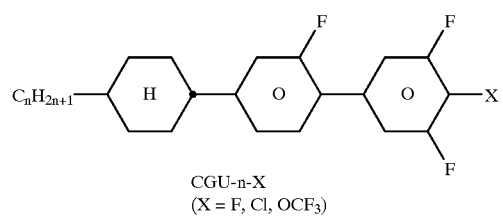
CGU-n-X
(X = F, Cl, OCF₃)
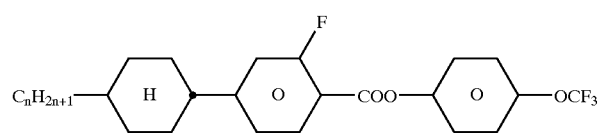
CGZP-n-OT
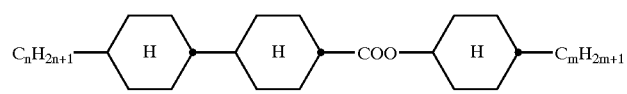
CH-nm
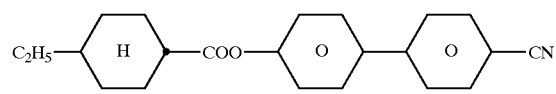
CHE TABLE B-continued
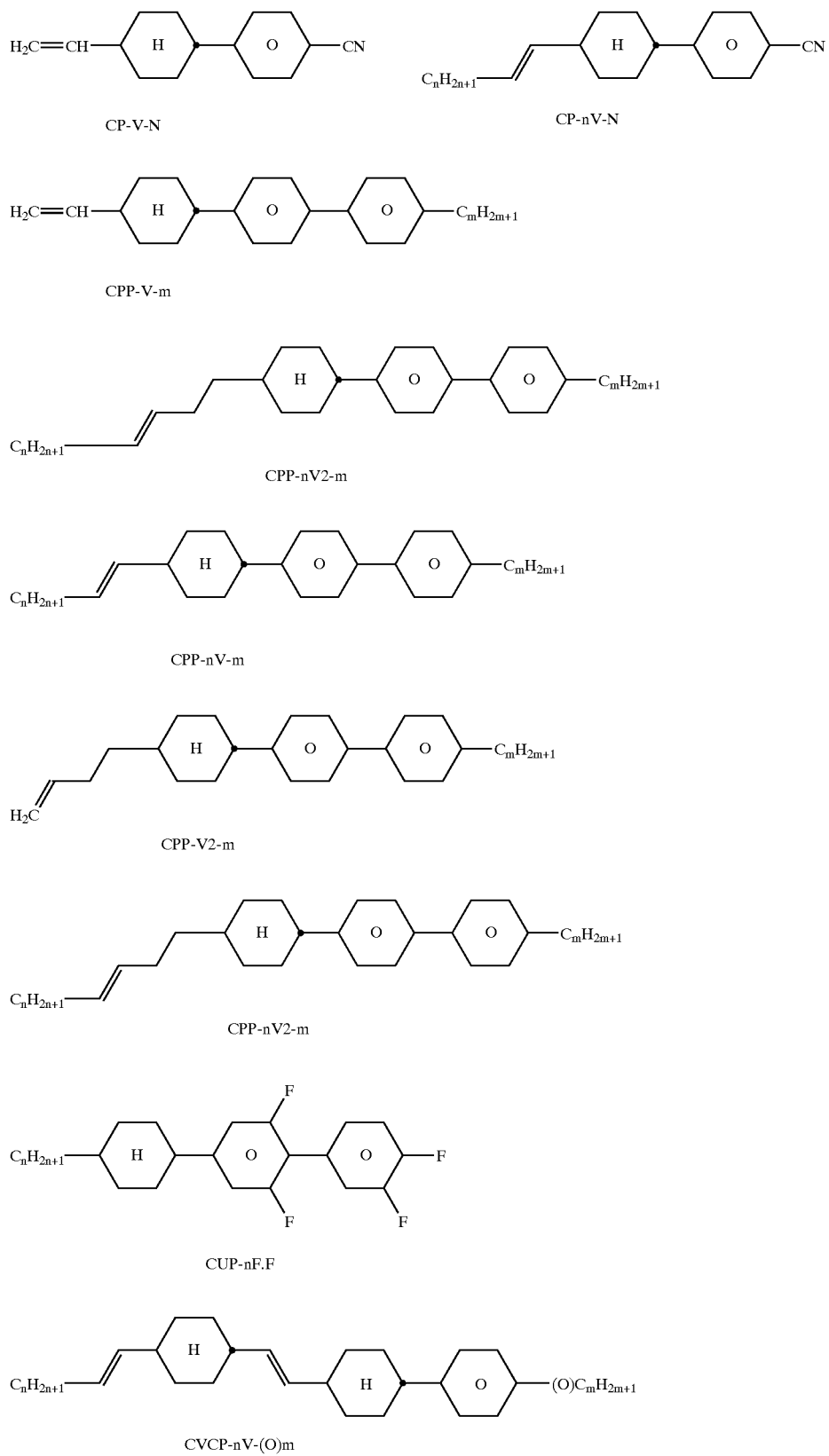

TABLE B-continued
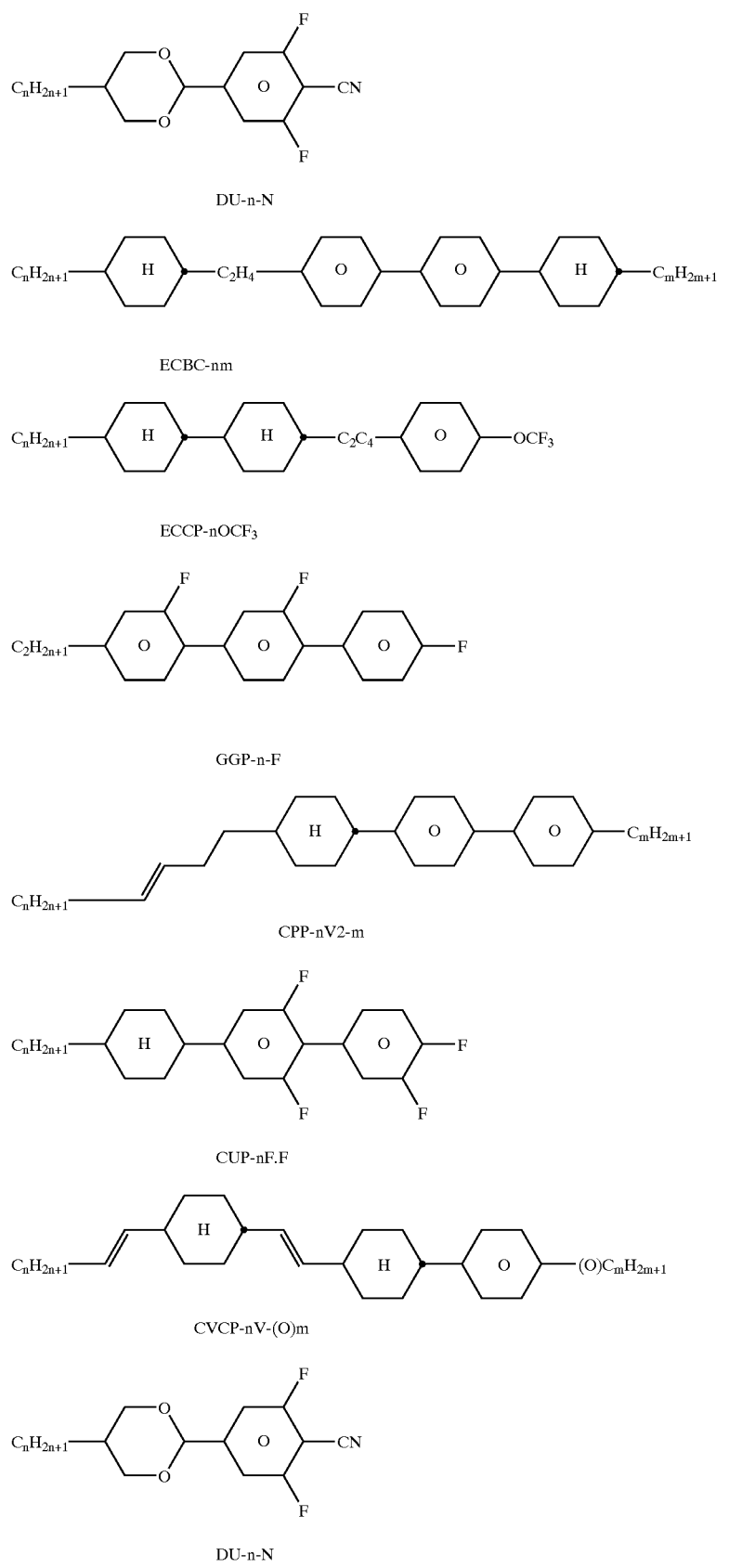

TABLE B-continued
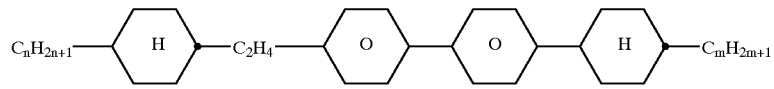
ECBC-nm
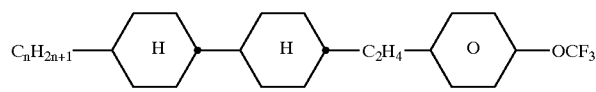
ECCP-nOCF₃
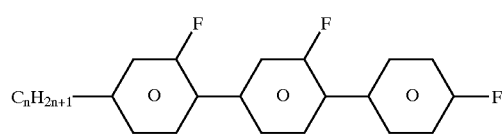
GGP-n-F
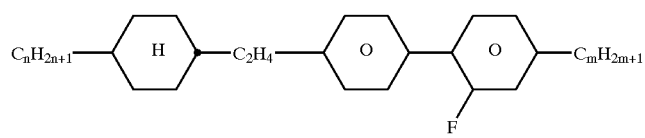
Inm
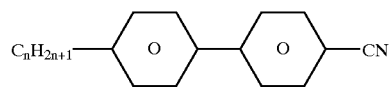
K3-n
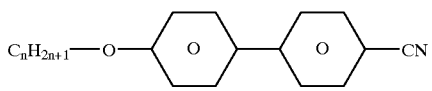
M3-n
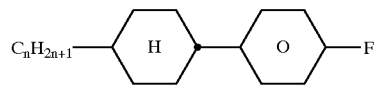
PCH-nF
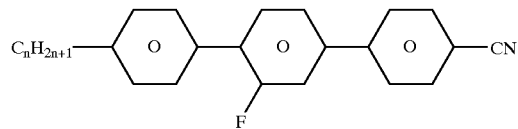
PGIP-n-N
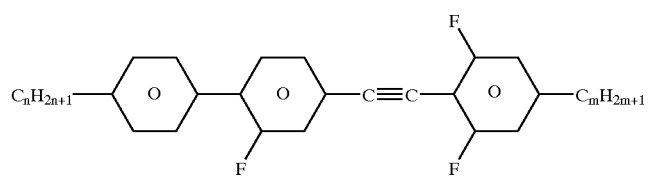
PPTUI-n-m TABLE B-continued
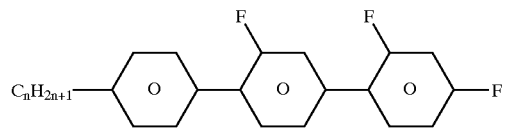
PGIGI-n-F
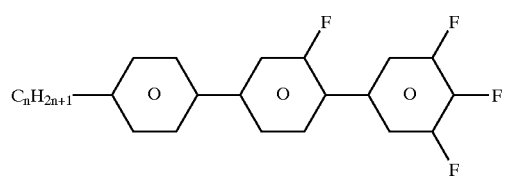
PGU-n-F
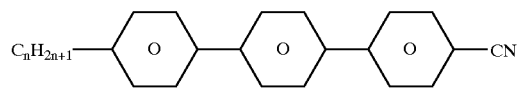
T3-n
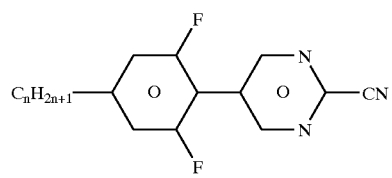
UM-n-N
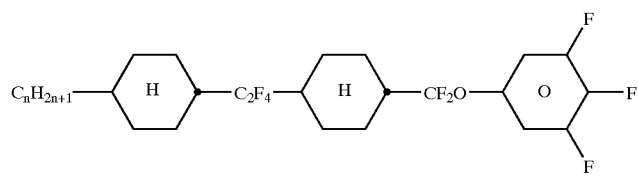
CWCQU-n-F
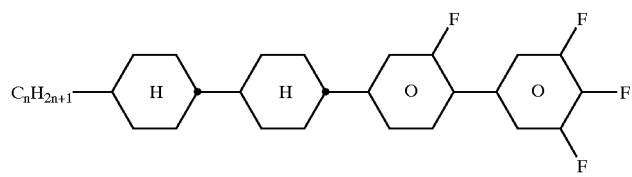
CCGU-n-F
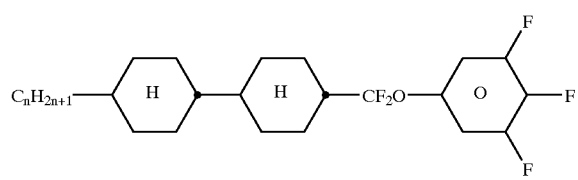
CCQU-n-F TABLE B-continued

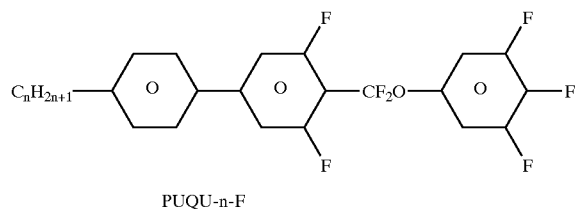

PUQU-n-F

The liquid-crystalline media according to the invention preferably contain seven or more, preferably nine or more, compounds selected from the group of compounds of Tables A and B and/or four or more, preferably five or more, compounds selected from the group of compounds of Table B and/or five or more, preferably six or more, compounds selected from the group of compounds of Table A.

Such compounds according to the invention and especially the liquid-crystalline media according to the invention are advantageously suitable for use in liquid-crystal display elements and as dielectric in electro-optical display elements, such as TN, STN and matrix liquid-crystal displays, especially those having an active matrix (AMD), such aus TFT displays or displays using MOS (Metal Oxide Semiconductor) transistors.

The examples below are intended to illustrate the invention without representing a limitation. Above and below, percentages are by weight. All temperatures are given in degrees Celsius.

In the preceding list and below, all temperatures are given in degrees Celsius. C=crystalline state, N=nematic phase and I=isotropic phase. The data between these symbols represent the transition temperatures. $\Delta\epsilon$ denotes the dielectric anisotropy (1 kHz, 20° C.), $\Delta\epsilon = \epsilon_\| - \epsilon_\perp$, where $\epsilon_\|$ is the dielectric constant parallel to the longitudinal axes of the molecule and $\epsilon_\perp$ is the dielectric constant perpendicular thereto. $\Delta n$ denotes the optical anisotropy (589 nm, 20° C.) and $n_o$ the refractive index. The flow viscosity $\nu_{20}$ (mm²/sec) and the rotational viscosity $\gamma_1$ (mPa·s) were each determined at 20° C. $V_{10}$, $V_{50}$ and $V_{90}$ denote the voltage for 10%, 50% and 90% transmission (viewing direction perpendicular to the plate surface). The electro-optical data were measured in a TN cell in the 1st minimum (i.e. at a d·$\Delta n$ value of 0.5) at 20° C., unless expressly stated otherwise.

"Conventional work-up" means that water is added if necessary, the mixture is adjusted to pH values between 2 and 10 depending on the structure of the final product, the mixture is extracted with a suitable solvent, such as dichloromethane, diethyl ether, methyl tert-butyl ether or toluene, the organic phase is separated, dried and evaporated, and the product is purified by distillation under reduced pressure or crystallization and/or chromatography.

1. SYNTHETIC EXAMPLES 1.1 Synthesis of 2-trifluoromethyl-6-(4'-n-propyl-cyclohexyl)-trans-decalin of the formula I.1.1

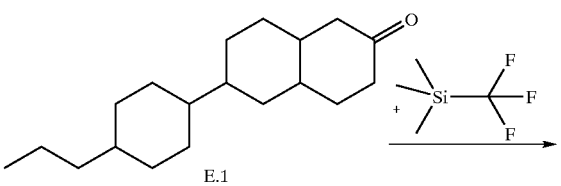

E.1

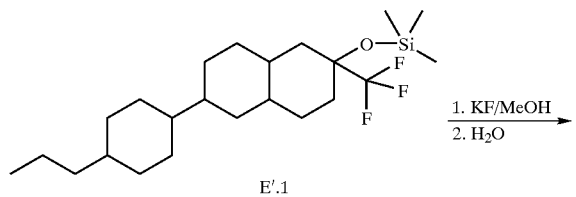

E'.1

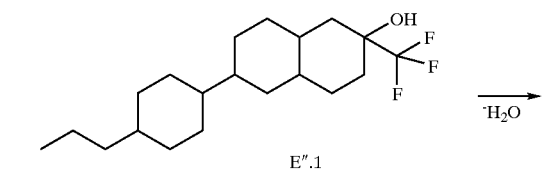

E".1

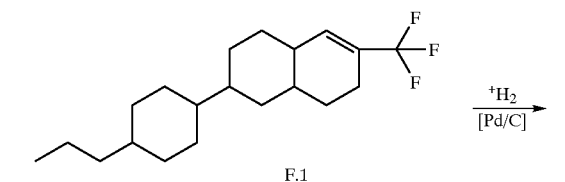

F.1

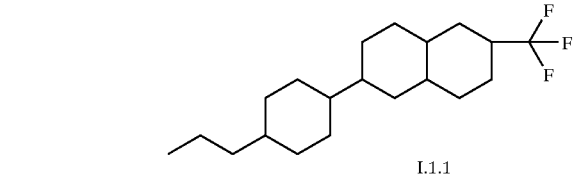

I.1.1

In the absence of water, a mixture of 0.044 mol of the decalinone of the formula E.1 and 0.049 mol of trifluoromethyltrimethylsilane in tetrahydrofuran is cooled down to 0° C. and 0.180 mol of tetrabutylammonium fluoride is added dropwise. The mixture is then allowed to warm to about 20° C. and stirred for another 2 hours. The mixture is then acidified with 20 ml of 18% strength hydrochloric acid solution and the organic phase is separated. The aqueous phase is extracted with 50 ml of methyl tert-butyl ether. The combined organic extracts are washed with sodium chloride solution and dried with sodium sulphate and the solvent is removed.

0.043 mol of the resulting intermediate of the formula E'.1 are dissolved in 100 ml of methanol and admixed with 500 mg of potassium fluoride, and the mixture is refluxed overnight and then subjected to conventional work-up.

Th resulting intermediate of the formula E".1 is dissolved in 70 ml of pyridine and thionyl chloride is slowly added dropwise to the solution at 0° C. The reaction mixture is stirred overnight and then subjected to conventional work-up.

0.103 mol of the product of the formula F.1 from the preceding step are hydrogenated in tetrahydrofuran with the addition of 9 g of 5% palladium on activated carbon. Removal of the solvent and recrystallization yields the desired product I.1.1.

(K 66 N (61.2) I; $\Delta\epsilon$=5.0; $\Delta n$=0.0374; $\nu_{20}$=38).

The compounds of the formula

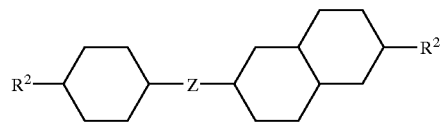

are prepared in a similar manner.

| $R^1$ | $R^2$ | Z | |
|---|---|---|---|
| —CF$_3$ | H | — | |
| —CF$_3$ | —CH$_3$ | — | |
| —CF$_3$ | —C$_2$H$_5$ | — | |
| —CF$_3$ | —C$_4$H$_9$ | — | |
| —CF$_3$ | —C$_5$H$_{11}$ | — | K 91 I; $\Delta\epsilon$ = 6.5; $\Delta n$ = 0.0420 |
| —CF$_3$ | —C$_6$H$_{13}$ | — | |
| —CF$_3$ | —C$_7$H$_{15}$ | — | |
| —C$_2$F$_5$ | —CH$_3$ | — | |
| —C$_2$F$_5$ | —C$_2$H$_5$ | — | |
| —C$_2$F$_5$ | —C$_3$H$_7$ | — | K 58 N 72.4 I; $\Delta\epsilon$ = 5.8; $\Delta n$ = 0.034 |
| —C$_2$F$_5$ | —C$_4$H$_9$ | — | |
| —C$_2$F$_5$ | —C$_5$H$_{11}$ | — | |
| —C$_2$F$_5$ | —C$_6$H$_{13}$ | — | |
| —C$_2$F$_5$ | —C$_7$H$_{15}$ | — | |
| —C$_3$F$_7$ | —CH$_3$ | — | |
| —C$_3$F$_7$ | —C$_2$H$_5$ | — | |
| —C$_3$F$_7$ | —C$_3$H$_7$ | — | $\Delta\epsilon$ = 4.8; $\Delta n$ = 0.034 |
| —C$_3$F$_7$ | —C$_4$H$_9$ | — | |
| —C$_3$F$_7$ | —C$_5$H$_{11}$ | — | |
| —C$_3$F$_7$ | —C$_6$H$_{13}$ | — | |
| —C$_3$F$_7$ | —C$_7$H$_{15}$ | — | |
| —CF$_3$ | H | | |
| —CF$_3$ | —CH$_3$ | —C$_2$F$_4$— | |
| —CF$_3$ | —C$_2$H$_5$ | —C$_2$F$_4$— | |
| —CF$_3$ | —C$_3$F$_7$ | —C$_2$F$_4$— | |
| —CF$_3$ | —C$_4$H$_9$ | —C$_2$F$_4$— | |
| —CF$_3$ | —C$_5$H$_{11}$ | —C$_2$F$_4$— | $\Delta\epsilon$ = 3.4; $\Delta n$ = 0.033 |
| —CF$_3$ | —C$_6$H$_{13}$ | —C$_2$F$_4$— | |
| —CF$_3$ | —C$_7$H$_{15}$ | —C$_2$F$_4$— | |
| —C$_2$F$_5$ | —CH$_3$ | —C$_2$F$_4$— | |
| —C$_2$F$_5$ | —C$_2$H$_5$ | —C$_2$F$_4$— | |
| —C$_2$F$_5$ | —C$_3$H$_7$ | —C$_2$F$_4$— | |
| —C$_2$F$_5$ | —C$_4$H$_9$ | —C$_2$F$_4$— | |
| —C$_2$F$_5$ | —C$_5$H$_{11}$ | —C$_2$F$_4$— | |
| —C$_2$F$_5$ | —C$_6$H$_{13}$ | —C$_2$F$_4$— | |
| —C$_3$F$_5$ | —C$_7$H$_{15}$ | —C$_2$F$_4$— | |
| —C$_3$F$_7$ | —CH$_3$ | —C$_2$F$_4$— | |
| —C$_3$F$_7$ | —C$_2$H$_5$ | —C$_2$F$_4$— | |
| —C$_3$F$_7$ | —C$_3$H$_7$ | —C$_2$F$_4$— | |
| —C$_3$F$_7$ | —C$_4$H$_9$ | —C$_2$F$_4$— | |
| —C$_3$F$_7$ | —C$_5$H$_{11}$ | —C$_2$F$_4$— | |
| —C$_3$F$_7$ | —C$_6$H$_{13}$ | —C$_2$F$_4$— | |
| —C$_3$F$_7$ | —C$_7$H$_{15}$ | —C$_2$F$_4$— | |

1.2 Synthesis of 2-trifluoromethoxy-6-(4'-n-propyl-cyclohexyl)-trans-decalin of the formula I.10.2

H$_7$C$_3$—[cyclohexyl]—[decalin]—OH →<sup>a</sup> H$_7$C$_3$—[cyclohexyl]—[decalin]—OCSSMe

G.2      H.2

↓ b

H$_7$C$_3$—[cyclohexyl]—[decalin]—OCF$_3$

I.10.2 a: KOtBu/CS$_2$/(MeO)$_2$SO$_2$
b: Pyridin/HF/NBS 1 mol of potassium tert-butoxide is dissolved in 3 l of tetrahydrofuran. A suspension of the decalinol of the formula G.2 in 1 l of tetrahydrofuran is added at about 20° C. and the mixture is stirred for 1 hour. After addition of 1 mol of carbon disulphide, the mixture is stirred for another hour. After addition of 1 mol of dimethyl sulphate, the mixture is again stirred for one hour. Finally the mixture is subjected to conventional work-up and the resulting raw product of the formula H.2 is crystallized from ethanol.

In the subsequent reaction step, a suspension of 0.5 mol of N-bromosuccinimide in 250 mol of dichloromethane is cooled down to −40° C. At this temperature, 4.4 mol of hydrogen fluoride dissolved in 50 ml of pyridine are added dropwise. The mixture is warmed to about 20° C. and a solution of 0.1 mol of the thioester of the formula H.2 in 150 ml of dichloromethane are added dropwise at 0° C. The mixture is stirred for one hour and then subjected to conventional work-up.

The resulting product of the formula I.10.2 produced the following values:

$\Delta\epsilon=4.0; \Delta n=0.044.$

The following novel compounds of the formula I, defined by $R^1$ and $R^2$, were likewise obtained in a similar manner by using the corresponding starting materials.

| $R^1$ | $R^2$ |
|---|---|
| —OCF$_3$ | —CH$_3$ |
| —OCF$_3$ | —C$_2$H$_5$ |
| —OCF$_3$ | —C$_4$H$_9$ |
| —OCF$_3$ | —C$_5$H$_{11}$ |
| —OCF$_3$ | —C$_6$H$_{13}$ |
| —OCF$_3$ | —C$_7$H$_{15}$ |

A solution of 0.155 mol of potassium tert-butoxide in 100 ml of tetrahydrofuran (THF) is added dropwise to a suspension of 0.155 mol of methoxymethyltriphenylphosphonium bromide in 200 ml of THF at −5 to 0° C. The mixture is stirred at 0° C. for 30 min and admixed with a solution of 0.15 mol of the decalinone of the formula E.3 in 100 ml of THF.

Following work-up, 0.155 mol of the ether J.3 are stirred overnight with 600 ml of toluene and 300 ml of formic acid at about 20° C. The organic phase is separated off and extracted three times with toluene and the combined organic phases are washed with saturated sodium chloride solution and NaHCO$_3$ solution.

The resulting cis/trans mixture of the aldehyde K.3 is dissolved in 450 ml of methanol, 2.2 ml of 3 M sodium hydroxide solution and the mixture is stirred at about 20° C. After 50 min, the mixture is cooled down to 0° C. and the resulting white precipitate is filtered off with suction, dried under reduced pressure and crystallized from methyl tert-butyl ether.

An initial charge of 0.07 mol of the aldehyde K.3 and 0.21 mol of sodium chlorodifluoroacetate in 220 ml of dimethylformamide are admixed with 0.15 mol of triphenylphosphine. The mixture is heated to 90° C. for 3 h. The mixture is then cooled down to about 20° C. and subjected to conventional work-up. The product of the formula I.6.3 produces the following values:

$\Delta\epsilon=1.8, \Delta n=0.062.$

The following novel compounds of the formula I, defined by $R^1$ and $R^2$, were likewise obtained in a similar manner by using the corresponding starting materials.

| $R^1$ | $R^2$ |
|---|---|
| CF$_2$=CF | —CH$_3$ |
| CF$_2$=CF | —C$_2$H$_5$ |
| CF$_2$=CF | —C$_3$H$_7$ |
| CF$_2$=CF | —C$_4$H$_9$ |
| CF$_2$=CF | —C$_5$H$_{11}$ |
| CF$_2$=CF | —C$_6$H$_{13}$ |
| CF$_2$=CF | —C$_7$H$_{15}$ |

1.3 Synthesis of 2-(2,2-difluorovinyl)-6-(4'-n-pentyl-cyclohexyl)-trans-decalin of the formula I.6.3

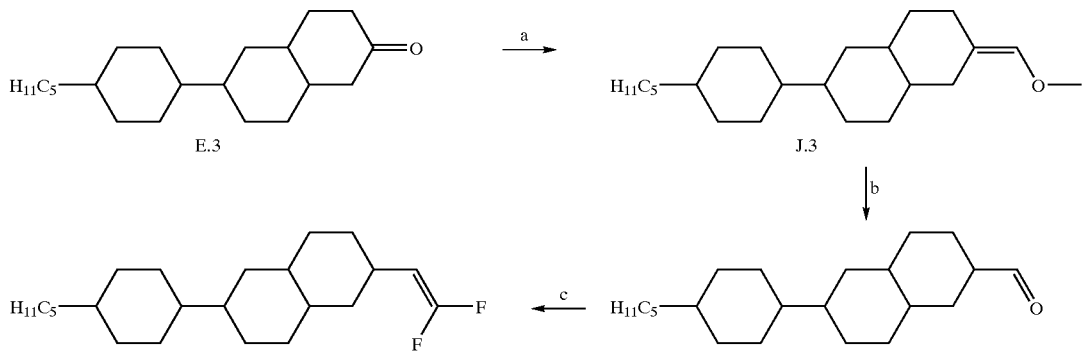

a: MeOCH=PPh$_3$
b: 1. H$_3$O$^+$; 2. cat. KOH, MeOH
c: ClCF$_2$COONa, PPh$_3$, DMF -continued

| R¹ | R² |
|---|---|
| CF₂=CF | —CH₃ |
| CF₂=CF | —C₂H₅ |
| CF₂=CF | —C₃H₇ |
| CF₂=CF | —C₄H₉ |
| CF₂=CF | —C₆H₁₃ |

-continued

| R¹ | R² |
|---|---|
| CF₂—CF—O | —C₄H₉ |
| CF₂—CF—O | —C₅H₁₁ |
| CF₂—CF—O | —C₆H₁₃ |
| CF₂—CF—O | —C₇H₁₅ |

1.4 Synthesis of 2-(2,2-difluorovinyloxy)-6-(4'-n-propyl-cyclohexyl)-trans-decalin of the formula I.12.4

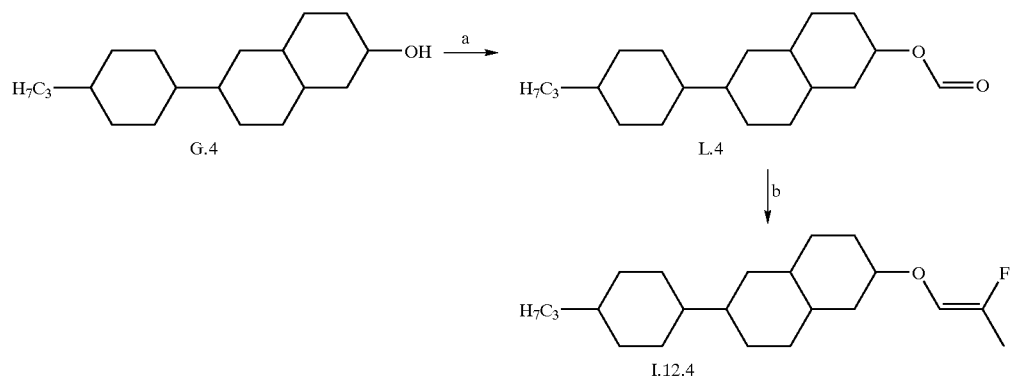

a: HCOOH/DCC/cat. DMAP
b CF₂Br₂/(Me₂N)₃P

A solution of 0.5 mol of the decalinol G.4 in 500 ml of dichloromethane is cooled down to −5° C. At this temperature, 0.5 mol of formic acid in 250 ml of dichloromethane are added dropwise. Subsequently, 0.05 mol of 4-dimethylaminopyridine are added and a solution of 0.6 mol of dicyclohexylcarbodiimide in 250 ml of dichloromethane is added dropwise at a maximum temperature of 5° C. The mixture is stirred overnight, admixed with 10 g of oxalic acid and subjected to conventional work-up.

A solution of 0.075 mol of the ester L.4 in 30 ml of tetrahydrofuran and 300 ml of 1,4-dioxane is cooled down to 5° C. 0.15 mol of dibromodifluoro-methane is added and 0.15 mol of hexamethyltriaminophoshine is added dropwise at a maximum temperature of 10° C. The mixture is subjected to conventional work-up and the compound I.12.4 is crystallized from heptane. The following values are obtained: Δε=6.1, Δn=0.084.

The following novel compounds of the formula I, defined by R¹ and R², were likewise obtained in a similar manner by using the corresponding starting materials.

| R¹ | R² |
|---|---|
| CF₂—CF—O | —CH₃ |
| CF₂—CF—O | —C₂H₅ |
| CF₂—CF—O | —C₃H₇ |
| CF₂—CF—O | —C₄H₉ |
| CF₂—CF—O | —C₅H₁₁ |
| CF₂—CF—O | —C₆H₁₃ |
| CF₂—CF—O | —C₇H₁₅ |
| CF₂—CF—O | —CH₃ |
| CF₂—CF—O | —C₂H₅ |

EXAMPLE M1

| | | | |
|---|---|---|---|
| BCH-3F.F | 10.80% | Clearing point [° C.]: | 87.2 |
| BCH-5F.F | 9.00% | Δn [589 nm, 20° C.]: | 0.0906 |
| ECCP-3OCF$_3$ | 4.50% | Δε [20° C., 1 kHz]: | 5.2 |
| ECCP-5OCF$_3$ | 4.50% | ν$_{20}$ [mm$^2$/s]: | 16 |
| CBC-33F | 1.80% | | |
| CBC-53F | 1.80% | | |
| CBC-55F | 1.80% | | |
| PCH-6F | 7.20% | | |
| PCH-7F | 5.40% | | |
| CCP-2OCF$_3$ | 7.20% | | |
| CCP-3OCF$_3$ | 10.80% | | |
| CCP-4OCF$_3$ | 6.30% | | |
| CCP-5OCF$_3$ | 9.90% | | |
| PCH-5F | 9.00% | | |

10.00%

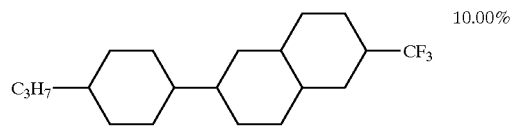

EXAMPLE M2

| | | | |
|---|---|---|---|
| CCH-3O1 | 11.20% | Clearing point [° C.]: | 73.9 |
| CCH-5O1 | 8.80% | Δn [589 nm, 20° C.]: | 0.0566 |
| CCP-2F.F.F | 8.00% | Δε [20° C., 1 kHz]: | 6.1 |
| CCP-3F.F.F | 10.40% | | |
| CCP-5F.F.F | 4.00% | | |
| CCZU-2-F | 4.00% | | |
| CCZU-3-F | 13.60% | | |
| CCZU-5-F | 4.00% | | |
| CH-33 | 2.40% | | |
| CH-35 | 2.40% | | |
| CH-43 | 2.40% | | |
| CCPC-33 | 2.40% | | |
| CCH-3CF$_3$ | 6.40% | | |

20.00%

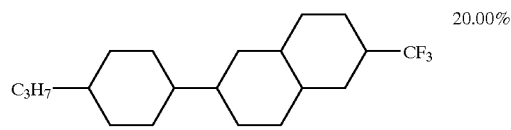

EXAMPLE M3

| | | | |
|---|---|---|---|
| PCH-5F | 3.20% | Clearing point [° C.]: | 98.1 |
| CCP-2OCF$_2$.F.F | 17.03% | | |
| CCP-3OCF$_2$.F.F | 15.99% | | |
| CCP-5OCF$_2$.F.F | 17.03% | | |
| CUP-2F.F | 5.36% | | |
| CUP-3F.F | 5.36% | | |
| CBC-33F | 5.36% | | |
| CBC-53F | 5.36% | | |
| CBC-55F | 5.28% | | |

20.05%

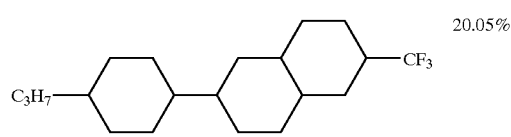

EXAMPLE M4

| | | | |
|---|---|---|---|
| CCP-2F.F.F | 11.0% | Clearing point [° C.]: | 79.0 |
| CCP-3F.F.F | 11.0% | Δn [589 nm, 20° C.]: | 0.0720 |
| CCP-5F.F.F | 6.0% | Δε [20° C., 1 kHz]: | +5.5 |
| CCZU-2-F | 5.0% | $V_{10}$ [V]: | 1.37 |
| CCZU-3-F | 15.0% | $V_{50}$ [V]: | 1.68 |
| CCZU-5-F | 4.0% | $V_{90}$ [V]: | 2.11 |
| CCP-2OCF$_3$.F | 7.0% | | |
| CCP-5OCF$_3$.F | 5.0% | | |
| CGU-2-F | 6.0% | | |
| CGU-3-F | 4.0% | | |
| CCOC-3-3 | 2.0% | | |
| CCOC-4-3 | 2.0% | | |
| CC-5-V | 9.0% | | |

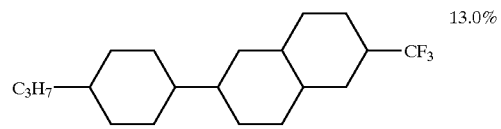 13.0%

EXAMPLE M5

| | | | |
|---|---|---|---|
| BCH-3F.F | 10.80% | Clearing point [° C.]: | 87.4 |
| BCH-5F.F | 9.00% | Δn [589 nm, 20° C.]: | 0.0915 |
| ECCP-30CF$_3$ | 4.50% | Δε [20° C., 1 kHz]: | +5.5 |
| ECCP.50CF$_3$ | 4.50% | $ν_{20}$ [mm$^2$/s$^1$] | 16 |
| CBC-33F | 1.80% | | |
| CBC-53F | 1.80% | | |
| CBC-55F | 1.80% | | |
| PCH-6F | 7.20% | | |
| PCH-7F | 5.40% | | |
| CCP-20CF$_3$ | 7.20% | | |
| CCP-30CF$_3$ | 10.80% | | |
| CCP-40CF$_3$ | 6.30% | | |
| CCP-50CF$_3$ | 9.90% | | |
| PCH-5F | 9.00% | | |

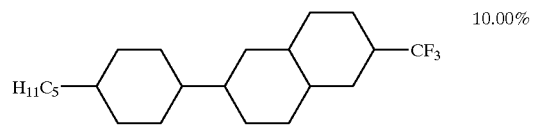 10.00%

EXAMPLE M6

| | |
|---|---|
| CCP-2F.F.F | 11.00% |
| CCP-3F.F.F | 13.00% |
| CCP-5F.F.F | 5.00% |
| CCP-2OCF$_3$.F | 7.00% |
| CCP-3OCF$_3$.F | 11.00% |
| CGU-3-F | 4.00% |
| CCOC-3-3 | 3.00% |
| CCOC-3-5 | 2.00% |
| CCOC-4-3 | 4.00% |
| CCH-3CF$_3$ | 8.00% |
| CCH-5CF$_3$ | 7.00% |

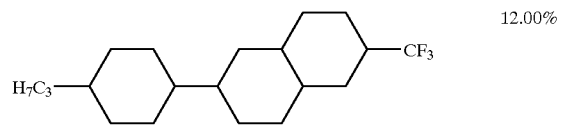 12.00%

-continued

| | |
|---|---|
| (structure) | 5.00% |
| CCGU-3-F | 8.00% |

EXAMPLE M7

| | |
|---|---|
| CCH-3CF$_3$ | 8.00% |
| CCH-5CF$_3$ | 6.00% |
| CCP-2F.F.F | 11.00% |
| CCP-3F.F.F | 13.00% |
| CCP-5F.F.F | 5.00% |
| CCZU-2-F | 4.00% |

| | |
|---|---|
| CCZU-3-F | 16.00% |
| CCZU-5-F | 4.00% |
| CCOC-33 | 3.00% |
| CCOC-3-5 | 3.00% |
| CCOC-4-3 | 4.00% |
| H₇C₃—⬡—⬡⬡—CF₃ | 12.00% |
| H₁₁C₅—⬡—⬡⬡—CF₃ | 5.00% |
| CCGU-3-F | 6.00% |

EXAMPLE M8

| | |
|---|---|
| CCP-2F.F.F | 11.00% |
| CCP-3F.F.F | 13.00% |
| CCP-5F.F.F | 6.00% |
| CCZU-2-F | 4.00% |
| CCZU-3-F | 16.00% |
| CCZU-5-F | 4.00% |
| H₇C₃—⬡—⬡⬡—CF₃ | 13.00% |
| H₁₁C₅—⬡—⬡⬡—CF₃ | 5.00% |
| CCGU-2-F | 6.00% |
| CCGU-3-F | 8.00% |
| CCOC-3-3 | 3.00% |
| CCOC-3-5 | 2.00% |
| CCOC-4-5 | 3.00% |
| CCGU-3-F | 6.00% |

EXAMPLE M9

| | | | |
|---|---|---|---|
| BCH-3F.F | 10.80% | Clearing point [° C.]: | +88.9 |
| BCH-5F.F | 9.00% | Δn [589 nm, 20° C.]: | 0.0908 |
| ECCP-30CF₃ | 4.50% | Δε [20° C., 1 kHz]: | +5.4 |
| ECCP.50CF₃ | 4.50% | | |
| CBC-33F | 1.80% | | |
| CBC-53F | 1.80% | | |
| CBC-55F | 1.80% | | |
| PCH-6F | 7.20% | | |
| PCH-7F | 5.40% | | |
| CCP-20CF₃ | 7.20% | | |
| CCP-30CF₃ | 10.80% | | |
| CCP-40CF₃ | 6.30% | | |
| CCP-50CF₃ | 9.90% | | |
| PCH-5F | 9.00% | | |

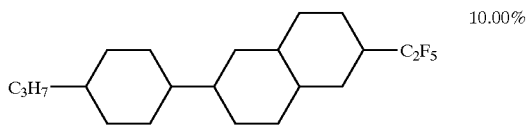

10.00%

EXAMPLE 10

| | | | |
|---|---|---|---|
| CCH-301 | 12.60% | Clearing point [° C.]: | +78.5 |
| CCH-3CF₃ | 7.20% | Δn [589 nm, 20° C.]: | +0.0582 |
| CCH-501 | 9.90% | Δε [20° C., 1 kHz]: | +6.3 |
| CCP-2F.F.F | 9.00% | K₃/K₁: | 1.14 |
| CCP-3F.F.F | 11.70% | | |
| CCP-5F.F.F | 4.50% | | |
| CCPC-33 | 2.70% | | |
| CCZU-2-F | 4.50% | | |
| CCZU-3-F | 15.30% | | |
| CCZU-5-F | 4.50% | | |
| CH-33 | 2.70% | | |
| CH-35 | 2.70% | | |
| CH-43 | 2.70% | | |

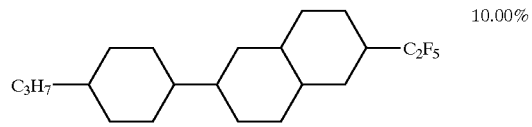

10.00%

EXAMPLE 11

| | |
|---|---|
| CCH-301 | 4.00% |
| CCH-501 | 10.00% |
| CCP-1F.F.F | 6.00% |
| CCP-2F.F.F | 10.00% |
| CCP-3F.F.F | 10.00% |
| CCP-5F.F.F | 5.00% |
| CCOC-3-3 | 3.00% |
| CCOC-4-3 | 4.00% |
| CCOC-3-5 | 2.00% |
| CH-35 | 3.00% |
| CWCQU-1-F | 7.00% |
| CWCQU-2-F | 7.00% |
| CWCQU-3-F | 8.00% |
| CCZU-2-F | 5.00% |
| CCZU-3-F | 7.00% |

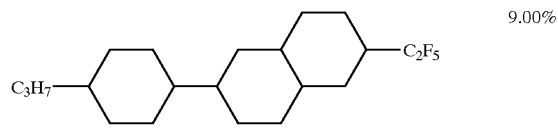

9.00%

EXAMPLE M12

| | |
|---|---|
| CCH-301 | 8.00% |
| CCH-501 | 11.00% |
| CCP-1F.F.F | 6.00% |
| CCP-2F.F.F | 10.00% |
| CCP-3F.F.F | 10.00% |
| CCP-5F.F.F | 6.00% |
| CCP-3OCF$_3$.F | 6.00% |
| CCP-5OCF$_3$.F | 4.00% |
| CCOC-3-3 | 2.00% |
| CCOC-3-5 | 2.00% |
| CCOC-4-3 | 3.00% |
| CWCQU-1-F | 6.00% |
| CWCQU-2-F | 6.00% |
| CWCQU-3-F | 7.00% |

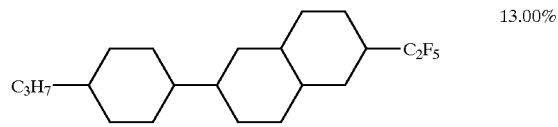

13.00%

EXAMPLE M13

| | |
|---|---|
| CCH-301 | 10.00% |
| CCH-501 | 13.00% |
| CCP-1F.F.F | 7.00% |
| CCP-2F.F.F | 10.00% |
| CCP-3F.F.F | 10.00% |
| CCP-5F.F.F | 5.00% |
| CCP-2OCF$_3$.F | 5.00% |
| CCP-3OCF$_3$.F | 9.00% |

-continued

| | |
|---|---|
| CCP-5OCF$_3$.F | 10.00% |
| CCOC-3-3 | 3.00% |
| CCOC-3-5 | 2.00% |
| CCOC-4-3 | 4.00% |

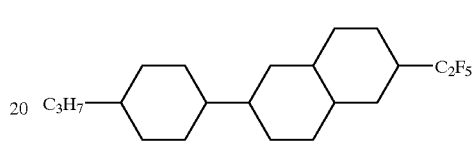

12.00%

EXAMPLE M14

| | |
|---|---|
| CCH-301 | 4.00% |
| CCH-501 | 5.00% |
| CCH-3CF$_3$ | 3.00% |
| CCH-5CF$_3$ | 5.00% |
| CCP-1F.F.F | 9.00% |
| CCP-2F.F.F | 11.00% |
| CCP-3F.F.F | 10.00% |
| CCP-5F.F.F | 5.00% |
| CCP-3OCF$_3$.F | 10.00% |
| CCP-5OCF$_3$.F | 10.00% |
| CCOC-3-3 | 3.00% |
| CCOC-3-5 | 3.00% |
| CCOC-4-3 | 4.00% |

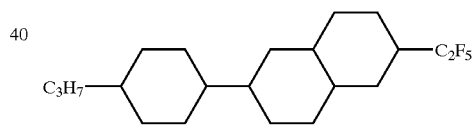

18.00%

What is claimed is:

1. A 2,4'-substituted 6-cyclohexyl-trans-decalin compound of the formula I

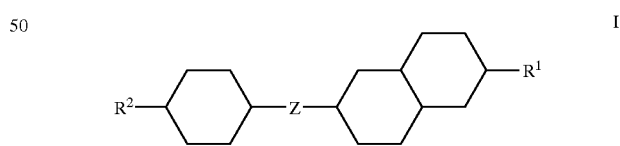

I in which $R^1$ is halogen or alkyl having 1 to 18 carbon atoms, in which, one or two non-adjacent CH$_2$ groups are optionally replaced by —O—, —S—, —CO—, —O—CO—, —CO—O—, —CHR$^3$—CHR$^4$— and/or —C≡C— and in which at least one H atom is replaced by a halogen atom, $R^2$ is H, halogen, —CN or alkyl having 1 to 18 carbon atoms, in which, one or two non-adjacent CH$_2$ groups are optically replaced by —O—, —S—, —CO—, —O—CO—, —CO—O—, -E- and/or —C≡C— and/or in which, one or more H atoms are optionally replaced by halogen, Z is a single bond, —CH$_2$O—, —OCH$_2$—, —COO—, —C≡C—, —CH═CH—, —CF$_2$O—, —OCF$_2$—, —CF═CF—, —C$_2$F$_4$—, —CH═CH—(CH$_2$)$_2$— or —(CH$_2$)$_4$—, and E is CR$^3$═CR$^4$ or CHR$^3$—CHR$^4$, and R$^3$, R$^4$ are each, independently of one another, H, alkyl having 1–6 carbon atoms, F, Cl, Br, CF$_3$ or CN.

2. A compound according to claim 1, wherein R$^2$ is H, methyl, ethyl, n-propyl, n-butyl, n-pentyl, n-hexyl, n-heptyl or n-octyl.

3. A compound according to claim 1, wherein R$^1$ contains two or more F-atoms.

4. A compound according of claim 1, wherein R$^1$ is perfluorinated.

5. A compound according of claim 1, wherein R$^1$ is alkyl, alkoxy, alkenyloxy, oxaalkyl or oxaalkenyl having 1 to 8 carbon atoms, where at least one H atom is substituted by a halogen atom and R$^2$ is alkyl, alkenyl, alkoxy, alkenyloxy, oxaalkyl or oxaalkenyl having 1 to 8 carbon atoms, wherein H atoms are optionally substituted by halogen.

6. A compound according of claim 1, wherein R$^1$ is —CF$_3$, —C$_2$F$_5$, —C$_3$F$_7$, or —OCF$_3$ and R$^2$ is —CF$_3$, —C$_2$F$_5$, —C$_3$F$_7$, —OCF$_3$, —CH═CHF, —(CH$_2$)$_n$—CH═CHF, —CH═CF$_2$, —(CH$_2$)$_n$—CH═CF$_2$, —CF═CF$_2$, —(CH$_2$)$_n$—CF═CF$_2$, —OCH═CHF, —OCH═CF$_2$ or —OCF═CF$_2$, where n is from 1 to 6.

7. Liquid-crystalline medium having two or more liquid-crystalline components, which it comprises at least one compound of the formula I according to one of claim 1.

8. Liquid-crystal display element, which it contains a liquid-crystalline medium according to claim 7.

9. Electro-optical display element, which it contains, as dielectric, a liquid-crystalline medium according to claim 7.

10. A compound according to claim 1, which compound exhibits a dielectric anisotropy, Δε, ≧4.0 and an optical anisotropy, Δn, ≧0.07.

11. A compound according to claim 1, wherein R$^1$ terminates in a CHF$_2$ or CF$_3$ group.

12. A compound according to claim 1, wherein Z is a single bond or —C$_2$F$_4$—.

13. A compound according to claim 1, which is of one of the following formulae:

I.1
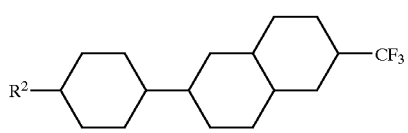

-continued

I.2
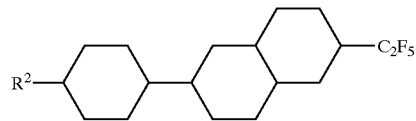

I.3
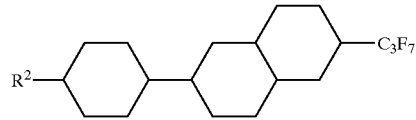

I.4
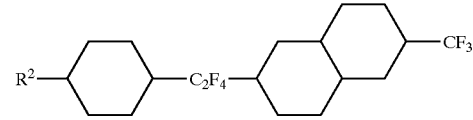

I.10
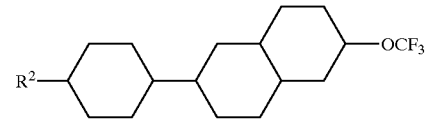

I.14
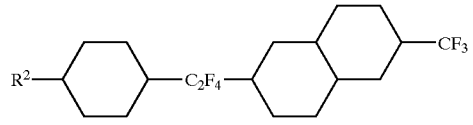

14. A liquid-crystalline medium of claim 7, wherein the medium contains 1 to 40% by weight of compounds of the formula I.

15. A liquid-crystalline medium of claim 7, wherein the medium contains 5 to 30% by weight of compounds of the formula I.

16. A liquid-crystalline medium of claim 7, wherein the medium contains 45 to 90% by weight of compounds of the formula I.

17. A liquid-crystalline medium of claim 7, wherein the medium contains two, three, four or five different compounds of formula I.

* * * * *

UNITED STATES PATENT AND TRADEMARK OFFICE
CERTIFICATE OF CORRECTION

PATENT NO. : 6,916,513 B2
DATED : July 12, 2005
INVENTOR(S) : Matthias Bremer

It is certified that error appears in the above-identified patent and that said Letters Patent is hereby corrected as shown below:

Column 51,
Line 33, reads "to one of claim 1" should read -- to claim 1 --.
Lines 34 and 36, delete the word "it".

Signed and Sealed this

Eighth Day of November, 2005

JON W. DUDAS
*Director of the United States Patent and Trademark Office*